United States Patent
Wu et al.

(10) Patent No.: US 9,815,056 B2
(45) Date of Patent: Nov. 14, 2017

(54) SINGLE SIDED LIGHT-ACTUATED MICROFLUIDIC DEVICE WITH INTEGRATED MESH GROUND

(71) Applicants: THE REGENTS OF THE UNIVERSITY OF CALIFORNIA, Oakland, CA (US); BERKELEY LIGHTS, INC., Emeryville, CA (US)

(72) Inventors: Ming-Chiang Wu, Moraga, CA (US); Jodi Tsu-An Loo, Agoura Hills, CA (US); Shao Ning Pei, Albany, CA (US); Gaetan L. Mathieu, Varennes (CA); Jian Gong, Danville, CA (US); Randall D. Lowe, Jr., Emeryville, CA (US); Justin K. Valley, Berkeley, CA (US)

(73) Assignees: THE REGENTS OF THE UNIVERSITY OF CALIFORNIA, Oakland, CA (US); BERKELEY LIGHTS, INC., Emeryville, CA (US)

( * ) Notice: Subject to any disclaimer, the term of this patent is extended or adjusted under 35 U.S.C. 154(b) by 0 days.

(21) Appl. No.: 14/960,010

(22) Filed: Dec. 4, 2015

(65) Prior Publication Data
US 2016/0158748 A1 Jun. 9, 2016

Related U.S. Application Data

(60) Provisional application No. 62/088,532, filed on Dec. 5, 2014.

(51) Int. Cl.
*B01L 99/00* (2010.01)
*B01L 3/00* (2006.01)
*G01N 27/447* (2006.01)

(52) U.S. Cl.
CPC ..... *B01L 3/50273* (2013.01); *B01L 3/502707* (2013.01); *B01L 3/502715* (2013.01);
(Continued)

(58) Field of Classification Search
CPC ........... B01L 3/50273; B01L 3/502715; B01L 3/502792; B01L 3/502707;
(Continued)

(56) References Cited

U.S. PATENT DOCUMENTS 5,814,200 A 9/1998 Pethig
6,294,063 B1 9/2001 Becker
(Continued)

FOREIGN PATENT DOCUMENTS

KR 2012006610 6/2012
WO 2009046125 4/2009
(Continued)

OTHER PUBLICATIONS

European Patent Office (EPO), International Search Report and Written Opinion dated Mar. 18, 2016, related PCT International Application No. PCT/US2015/064074, pp. 1-10, with claims searched, pp. 11-23.

(Continued)

*Primary Examiner* — Paul Hyun
(74) *Attorney, Agent, or Firm* — O'Banion & Ritchey LLP; John P. O'Banion

(57) ABSTRACT

Single-sided optoelectrowetting (SSOEW)-configured substrates are provided, as well as microfluidic devices that include such substrates. The substrates can include a planar electrode, a photoconductive (or photosensitive) layer, a dielectric layer (single-layer or composite), a mesh electrode, and a hydrophobic coating. Fluid droplets can be moved across the hydrophobic coating of such substrates in a light-actuated manner, upon the application of a suitable
(Continued)

AC voltage potential across the substrate and the focusing of light into the photoconductive layer of the substrate in a location proximal to the droplets. Walls can be disposed upon the substrates to form the microfluidic devices. Together the walls and substrate can form a microfluidic circuit, through which droplets can be moved.

30 Claims, 9 Drawing Sheets

(52) U.S. Cl.
CPC .. *B01L 3/502792* (2013.01); *G01N 27/44704* (2013.01); *G01N 27/44743* (2013.01); *G01N 27/44791* (2013.01); *B01L 2200/06* (2013.01); *B01L 2300/0654* (2013.01); *B01L 2300/0816* (2013.01); *B01L 2300/0858* (2013.01); *B01L 2300/0877* (2013.01); *B01L 2300/12* (2013.01); *B01L 2300/165* (2013.01); *B01L 2400/0427* (2013.01)

(58) Field of Classification Search
CPC ......... B01L 2300/0816; B01L 2200/06; B01L 2300/0877; B01L 2300/12; B01L 2300/165; G01N 27/44704; G01N 27/44791; G01N 27/44743
See application file for complete search history.

(56) References Cited

U.S. PATENT DOCUMENTS

| | | | |
|---|---|---|---|
| 6,565,727 B1 | 5/2003 | Shenderov | |
| 6,911,132 B2 | 6/2005 | Pamula | |
| 6,942,776 B2 | 9/2005 | Medoro | |
| 7,090,759 B1 | 8/2006 | Seul | |
| 7,547,380 B2 | 6/2009 | Velev | |
| 9,182,591 B2* | 11/2015 | Crane | G02B 26/005 |
| 2002/0088712 A1 | 7/2002 | Miles | |
| 2003/0224528 A1 | 12/2003 | Chiou | |
| 2004/0231987 A1 | 11/2004 | Sterling | |
| 2005/0175981 A1 | 8/2005 | Voldman | |
| 2005/0266571 A1 | 12/2005 | Stout | |
| 2007/0095669 A1 | 5/2007 | Lau | |
| 2007/0138016 A1 | 6/2007 | Wang | |
| 2007/0139486 A1 | 6/2007 | Decre | |
| 2007/0242105 A1 | 10/2007 | Srinivasan | |
| 2008/0000635 A1 | 1/2008 | Rioufol | |
| 2008/0302732 A1 | 12/2008 | Soh | |
| 2009/0170186 A1* | 7/2009 | Wu | B03C 5/026 435/286.1 |
| 2010/0101960 A1 | 4/2010 | Ohta | |
| 2010/0120130 A1* | 5/2010 | Srinivasan | B01F 13/0071 435/283.1 |
| 2010/0181195 A1 | 7/2010 | Garcia Tello | |
| 2011/0005931 A1 | 1/2011 | Zhe | |
| 2011/0042220 A1* | 2/2011 | Wang | B01L 3/502792 204/643 |
| 2011/0095201 A1 | 4/2011 | Stolowitz | |
| 2012/0015382 A1 | 1/2012 | Weitz | |
| 2012/0024708 A1 | 2/2012 | Chiou | |
| 2012/0091003 A1* | 4/2012 | Chuang | B03C 5/02 204/547 |
| 2012/0325665 A1 | 12/2012 | Chiou | |
| 2013/0118905 A1 | 5/2013 | Morimoto | |
| 2013/0206597 A1 | 8/2013 | Wang | |
| 2014/0102900 A1 | 4/2014 | Akella | |
| 2014/0116881 A1 | 5/2014 | Chapman | |
| 2015/0107995 A1 | 4/2015 | Sista | |
| 2015/0151298 A1 | 6/2015 | Hobbs | |
| 2016/0108432 A1* | 4/2016 | Punnamaraju | C12M 33/00 435/471 |
| 2016/0184821 A1 | 6/2016 | Hobbs | |

FOREIGN PATENT DOCUMENTS

| | | |
|---|---|---|
| WO | 2014167858 | 10/2014 |
| WO | 2015164846 | 10/2015 |
| WO | 2015164847 | 10/2015 |

OTHER PUBLICATIONS

Nevill, J. Tanner et al., "Integrated microfluidic cell culture and lysis on a chip", Lab on a Chip 7:1689-95 (2007), published online Oct. 19, 2007.

Gel, M. , "Microorifice-Based High-Yield Fusion on Microfluidic Chip: Electrofusion of Selected Pairs and Fusant Viability", IEEE Transactions on Nanosciences 8(4):300-05, Dec. 2009.

Park, Sung-Yong et al., "Single-sided continuous optoelectrowetting (SCOEW) for droplet manipulation with light patterns", Lab on a Chip, vol. 10, No. 13, pp. 1655-1661, Jul. 7, 2010, published online May 6, 2010.

Dalvi, Vishwanath H. et al., "Molecular Origins of Fluorocarbon Hydrophobicity", Proceedings of the National Academy of Sciences, vol. 107, No. 31, pp. 13603-13607, Aug. 3, 2010.

Xu, Guolin et al,. "Recent Trends in Dielectrophoresis", Informacije MIDEM, 2010, vol. 40, Issue No. 4, pp. 253-262.

Valley et al., "A unified platform for optoelectrowetting and optoelectronic tweezers", Lab on a Chip 11:1292-1297, Feb. 11, 2011.

Huang, H-Y et al., "Digital Microfluidic Dynamic Culture of Mammalian Embryos on an Electrowetting on Dielectric (EWOD) Chip", PLOS One 10(5): e0124196, doi:10.1371, joumla.pone. 0124196, May 1, 2015.

* cited by examiner

US 9,815,056 B2

SINGLE SIDED LIGHT-ACTUATED MICROFLUIDIC DEVICE WITH INTEGRATED MESH GROUND

CROSS REFERENCE TO RELATED APPLICATION(S)

This application claims priority to, and the benefit of, U.S. provisional patent application Ser. No. 62/088,532 filed on Dec. 5, 2014, incorporated herein by reference in its entirety.

STATEMENT REGARDING FEDERALLY SPONSORED RESEARCH OR DEVELOPMENT

Not Applicable

TECHNICAL FIELD

The present invention relates generally to microfluidic devices having an opto-eletrowetting (OEW) configuration. In particular, the present disclosure relates to single-sided opto-electrowetting (SSOEW) devices having an integrated mesh ground.

BACKGROUND

Micro-objects, such as biological cells, can be processed in microfluidic devices. For example, droplets containing micro-objects or reagents can be moved around and merged within a microfluidic device. Embodiments of the present invention are directed to improvements in microfluidic devices that facilitate carrying out complex chemical and biological reactions. Droplets can be moved and merged on or within a microfluidic device by changing an effective wetting property of an electrowetting surface in the microfluidic device. Such movements can facilitate, for example, workflows in which cells are processed to assess various cellular properties. Microfluidic devices having an electrowetting configuration typically include a hard cover, which can complicate the introduction of droplets onto and their removal from the electrowetting surface. Accordingly, it is desirable to have microfluidic devices that have a more accessible electrowetting surface.

SUMMARY OF THE INVENTION

Embodiments of the present invention provide novel, single-sided opto-electrowetting (SSOEW) devices having an integrated mesh ground. Any such SSOEW devices can form the base of a microfluidic device of the invention, and the microfluidic device can optionally include channels and/or chambers through which fluid can flow. The walls of the channels and/or chambers can be attached at their base to the top surface of the SSOEW device, and the channels and/or chambers can be enclosed or open at their top.

Additional embodiments of the invention provide methods of moving one or more droplets over the top surface of a SSOEW device of the invention. The one or more droplets (e.g., aqueous droplets) can have a volume that ranges from picoliters to microliters. Movement of a droplet can be controlled by projecting structured electromagnetic radiation (e.g., light) on a photoconductive layer of the SSOEW device, at a location beneath a leading edge of the droplet. The structured electromagnetic radiation modulates the electro-wetting characteristics of the top surface of the SSOEW device and can thereby generate a gradient in the surface tension of the droplet. By changing the position of the projected structured electromagnetic radiation, the droplet can be made to follow the electromagnetic radiation (e.g., in a circular pattern, a rectangular pattern, an irregular pattern, or any combination thereof).

Accordingly, in one aspect, the invention provides a substrate having a SSOEW configuration. The SSOEW-configured substrate can include a planar electrode, a photoconductive layer, a dielectric layer, a mesh ground electrode, and a hydrophobic coating. The photoconductive layer can be interposed between the planar electrode and the dielectric layer, with a bottom surface of the photoconductive layer adjoining a top surface of the planar electrode and a top surface of the photoconductive layer adjoining a bottom surface of the dielectric layer. The mesh ground electrode can adjoin a top surface of the dielectric layer or can be embedded within the dielectric layer; and the hydrophobic coating can coat the top surface of the dielectric layer and, depending upon its location, the top surface of the mesh ground electrode. The planar electrode and the mesh ground electrode can be configured to be connected to an AC voltage source (i.e., to opposing terminals of an AC voltage source) such that, when so connected, the SSOEW-configured substrate is capable of generating an optically actuated electrowetting (EW) force to aqueous droplets resting on or otherwise in contact with the hydrophobic coating of the substrate. In certain embodiments, the SSOEW-configured substrate is part of a microfluidic device. In certain embodiments, the microfluidic device is a nanofluidic device.

In certain embodiments, the planar electrode includes a metal conductor. For example, the planar electrode can include an indium-tin-oxide (ITO) layer (e.g., ITO-coated glass). In certain embodiments, the planar electrode comprises a non-metal conductor, such as conductive silicon (e.g., highly n- or p-doped silicon). Regardless, the metal or non-metal conductor should be thick enough to effectively conduct electrical current. Typically, a layer of conductive silicon will be at least 500 microns (e.g., about 500 to 1000 microns, about 550 to 800 microns, or about 600 to 700 microns) thick. In certain embodiments, the planar electrode includes both metal conductor and non-metal conductor elements. For example, the planar electrode can include a layer of conductive silicon with a layer of conductive metal (e.g., gold, silver, ITO) on the underside of the conductive silicon layer.

In certain embodiments, the photoconductive layer comprises hydrogenated amorphous silicon (a-Si:H). The photoconductive layer can have a thickness of at least 100 nm (e.g., at least 250 nm, 500 nm, 750 nm, 1000 nm, or more). In certain embodiments, the photoconductive layer can have a thickness of about 500 nm to 1500 nm (e.g., about 600 nm to about 1400 nm, about 700 nm to about 1300 nm, about 800 nm, to about 1200 nm, about 900 nm to about 1100 nm, or about 1000 nm).

In certain embodiments, the dielectric layer comprises a metal oxide, such as aluminum oxide or hafnium oxide. In certain embodiments, the dielectric layer has a thickness of at least 50 nm (e.g., at least about 75 nm, 100 nm, 125 nm, 150 nm, or more). For example, the dielectric layer can have a thickness of about 50 to about 250 nm (e.g., about 75 nm to about 225 nm, or about 100 nm to about 200 nm, or about 125 nm to about 175 nm, or about 140 nm to about 160 nm). In certain embodiments, the dielectric layer has been formed by atomic layer deposition. In certain embodiments, the dielectric layer has an impedance of about 10 to 50 kOhms.

In certain embodiments, the dielectric layer is a composite dielectric layer. For example, the dielectric layer can have at least a first dielectric layer and a second dielectric layer. The bottom surface of the first dielectric layer can be adjoining the photoconductive layer. In certain embodiments, the mesh ground electrode is interposed between the first dielectric layer and the second dielectric layer. The composite dielectric layer can have a thickness of at least about 50 nm (e.g., at least about 75 nm, 100 nm, 125 nm, 150 nm, or more). For example, the dielectric layer can have a thickness of about 50 to about 250 nm (e.g., about 75 nm to about 225 nm, about 100 nm to about 200 nm, about 125 nm to about 175 nm, or about 140 nm to 160 nm). In certain embodiments, the composite dielectric layer has an impedance of about 10 to 50 kOhms.

In certain embodiments, the each of the first and second dielectric layers of a composite dielectric layer comprise a metal oxide, such as aluminum oxide or hafnium oxide. One or both of the first and second dielectric layers can be formed by atomic layer deposition. In such embodiments, the first dielectric layer can have a thickness of at least about 100 nm (e.g., at least about 125 nm, about 150 nm, or more). For example, the first dielectric layer can have a thickness of about 125 nm to about 175 nm (e.g., about 140 nm to about 160 nm). In such embodiments, the second dielectric layer can have a thickness of about 50 nm or less (e.g., about 40 nm, about 30 nm, about 25 nm, about 20 nm, about 15 nm, about 10 nm, about 9 nm, about 8 nm, about 7 nm, about 6 nm, about 5 nm, about 4 nm, about 3 nm, or less). In certain embodiments, the first dielectric layer has a thickness of at least 125 nm (e.g., at least 150 nm) and the second dielectric layer has a thickness of 10 nm or less than 10 nm, (e.g., 5 nm or less).

In certain embodiments, the first dielectric layer of a composite dielectric layer has a lattice shape of substantially uniform thickness, with a top surface of the first dielectric layer adjoining a bottom surface of the mesh ground electrode and the mesh ground electrode interposed between the first dielectric layer and the second dielectric layer. The top surface of the first dielectric layer can be substantially contiguous with the bottom surface of the mesh ground electrode. In such embodiments, the first dielectric layer can comprise a metal oxide, such as aluminum oxide or hafnium oxide, and can have a thickness of at least about 50 nm (e.g., at least about 75 nm, about 100 nm, about 125 nm, about 150 nm, or more). For example, the first dielectric layer can have a thickness of about 50 nm to about 200 nm (e.g., about 75 nm to about 180 nm, about 100 nm to about 160 nm, or about 125 nm to about 150 nm). In such embodiments, the second dielectric layer can comprise a non-metal oxide, such as silicon oxide, and can have a variable thickness. For example, the second dielectric layer can have first regions, contacting the top surface of the photoconductive layer, having a thickness substantially the same as the thickness of the composite dielectric layer, and second regions, directly over the wires of the mesh ground electrode, having a thickness of about 50 nm or less (e.g., about 40 nm or less, about 30 nm or less, about 25 nm or less, about 20 nm or less, about 15 nm or less, about 10 nm or less, about 9 nm or less, about 8 nm or less, about 7 nm or less, about 6 nm or less, about 5 nm or less, about 4 nm or less, or about 3 nm or less). In certain embodiments, the first dielectric layer has a thickness of at least 125 nm (e.g., at least 150 nm) and the second dielectric layer has a thickness, directly over the wired of the mesh ground electrode of 10 nm or less (e.g., 5 nm or less).

In certain embodiments, the first dielectric layer of a composite dielectric layer is made from a first material having a dielectric constant $\in_1$ and the second dielectric layer is made from a second material having a dielectric constant $\in_2$, where $\in_1$ is different than $\in_2$. For example, $\in_1$ can be less than $\in_2$. For example, the first material can be a metal oxide, such as aluminum oxide or hafnium oxide, and the second material can be a non-metal oxide, such as silicon oxide.

In certain embodiments, the composite dielectric layer comprises a first dielectric layer, a second dielectric layer, and a third dielectric layer. The second dielectric layer can be interposed between the first and third dielectric layers. In certain embodiments, the first and third dielectric layers each comprise a metal oxide, such as aluminum oxide. In such embodiments, one or both of the first and third dielectric layers may have been formed by atomic layer deposition. The first dielectric layer can have a thickness of at least about 10 nm (e.g., about 10 nm to about 20 nm). In addition, the third dielectric layer can have a thickness of at least about 10 nm (e.g., about 10 nm to about 20 nm). In related embodiments, the second dielectric layer can comprise a non-metal oxide or a nitride. The non-metal oxide can be, for example, silicon oxide. The second dielectric layer can be formed by plasma enhanced chemical vapor deposition and can have a thickness of at least about 75 nm (e.g., at least about 100 nm, at least about 125 nm, at least about 150 nm, or more). For example, the second dielectric layer can have a thickness of about 100 nm to about 200 nm (e.g., about 125 nm to about 175 nm).

In certain embodiments, the first dielectric layer of a three-layer composite dielectric layer has a top surface adjoining a bottom surface of the mesh ground electrode, and the third dielectric layer has a bottom surface adjoining a top surface of the mesh ground electrode. Thus, for example, the mesh ground electrode can be entirely encased within the composite dielectric layer, with the second dielectric layer filling the spaces formed between the lateral edges of the wires of the mesh ground electrode.

In certain embodiments, the first dielectric layer of a three-layer composite dielectric layer is made from a first material that has a dielectric constant the second dielectric layer is made from a second material that has a dielectric constant $\in_2$, the third dielectric layer is made from a third material that has a dielectric constant $\in_3$, and $\in_1$ is different than $\in_3$. For example, $\in_1$ can be less than $\in_3$. In certain related embodiments, $\in_2$ can be less than $\in_3$ (e.g., $\in_2$ can have a value equal to or greater than $\in_1$ but less than $\in_3$). In certain embodiments, the three-layer composite dielectric layer has an impedance of about 10 to 50 kOhms.

In certain embodiments, the mesh ground electrode comprises a plurality of wires arranged in a lattice shape. The mesh ground electrode can further comprise plates located on top of vertices formed by wires of the mesh ground electrode. The plates, for example, can have substantially the same composition as the wires of the mesh ground electrode. In certain embodiments, the wires of the mesh ground electrode have a substantially square shape or a substantially rectangular shape (viewed in cross-section). Thus, the wires can have an average width and an average height. The average height of the wires can be at least about 50 nm (e.g., at least about 60 nm, about 70 nm, about 80 nm, about 90 nm, about 100 nm, or more). The average width of the wires can be at least about 100 nm (e.g., at least about 200 nm, about 300 nm, about 400 nm, about 500 nm, about 600 nm, about 700 nm, about 800 nm, about 900 nm, about 1000 nm, or more). In other embodiments, the wires of the mesh ground electrode can have a T-shape (viewed in cross section).

In certain embodiments, the mesh ground electrode comprises a conductive material, such as a metal (e.g., gold, aluminum, chromium, titanium, or combinations thereof). In certain embodiments, the mesh ground electrode comprises a layer of gold and an underlying layer of chromium or titanium. In certain embodiments, the conductive material is a semiconductor material that is highly electrically conductive (e.g., highly-doped silicon). In certain embodiments, the conductive material of the mesh ground electrode has an oxidized outer surface. For example, the mesh ground electrode can comprise aluminum that has an oxidized outer surface.

In certain embodiments, the mesh ground electrode has a linear fill factor β that is less than or equal to about 10% (e.g., about 9%, about 8%, about 7%, about 6%, about 5%, about 4%, about 3%, about 2%, about 1%, about 0.5%, or less). In certain embodiments, the wires of the mesh ground electrode have a pitch of less than 1 mm (e.g., about 200 microns to about 500 microns). In certain embodiments, the wires of the mesh ground electrode have a pitch of about 1.5 mm to 2 mm, about 1.0 mm to 1.5 mm, about 0.5 mm to 1.0 mm, about 400 to 800 microns, about 300 to 600 microns, about 200 to 400 microns, about 100 to 200 microns, about 50 to 100 microns, or about 10 to 50 microns.

In certain embodiments, the hydrophobic coating has a bottom surface that adjoins some or all of the top surface of the dielectric layer. In certain related embodiments, the bottom surface of the hydrophobic coating adjoins the top surface (and, optionally, the lateral surfaces of the wires) of the mesh ground electrode. Thus, the bottom surface of the hydrophobic coating can adjoin both the top surface of the dielectric layer and surfaces of the mesh ground electrode that do not adjoin the dielectric layer.

In certain embodiments, the hydrophobic coating can comprise an organofluorine polymer. The organofluorine polymer can have, for example, at least one perfluorinated segment. The organofluorine polymer can comprise, for example, polytetrafluoro-ethylene (PTFE). Alternatively, the organofluorine polymer can comprise poly(2,3-difluoromethylenyl-perfluorotetrahydrofuran). In such embodiments, the hydrophobic coating can have a thickness of at least about 10 nm, about 15 nm, about 20 nm, about 25 nm, about 30 nm, about 35 nm, or more.

In certain embodiments, the hydrophobic layer comprises a densely packed monolayer of amphiphilic molecules covalently bonded to molecules of the dielectric layer. The amphiphilic molecules of the hydrophobic layer can each comprise a siloxane group, a phosphonic acid group, or a thiol group, and the respective siloxane groups, phosphonic acid groups, and thiol groups can be covalently bonded to the molecules of the dielectric layer. In such embodiments, the hydrophobic layer can have a thickness of less than 5 nm (e.g., a thickness of about 1.5 to 3.0 nm).

In certain embodiments, the amphiphilic molecules of the hydrophobic layer comprise long-chain hydrocarbons. Thus, for example, the amphiphilic molecules can be alkyl-terminated siloxane, alkyl-terminated phosphonic acid, or alkyl-terminated thiol molecules. The long chain hydrocarbons can be unbranched, and can comprise a chain of at least 10 carbons (e.g., at least 16, 18, 20, 22, or more carbons). The alkyl-terminated siloxane can comprise trimethoxysilane, triethoxysilane, or triclorosilane. For example, the alkyl-terminated siloxane can be selected from the group consisting of octadecyltrimethoxysilane, octadecyltriethoxysilane, or octadecyltriclorosilane. In certain embodiments, the amphiphilic molecules of the hydrophobic layer can comprise fluorinated carbon chains. The fluorinated carbon chains have the chemical formula $CF_3-(CF_2)_m-(CH_2)_n-$, wherein m is at least 2, n is at least 2, and m+n is at least 9.

For example, m can be 7 (or greater) and n can be 2 (or greater). In certain embodiments, the hydrophobic layer is patterned such that select regions are relatively hydrophilic compared to the remainder of the hydrophobic layer.

In another aspect, the invention provides a microfluidic device having a base that includes a substrate having a SSOEW configuration, and walls disposed on the base. The base and the walls can together define a microfluidic circuit. The microfluidic device can optionally include a cover, which can be disposed on the walls. The SSOEW-configured substrate of the base can be any of the SSOEW-configured substrates described herein.

In certain embodiments, the walls comprise a structural polymer. The polymer can be a silicon-based polymer, such as polydimethylsiloxane (PDMS) or photo-patternable silicone (PPS). Alternatively, the walls can comprise an epoxy-based adhesive, such as SU-8. For microfluidic devices that include a cover, the cover can comprise the same structural polymer contained in the walls. In addition, the cover can be integral with the walls. Alternatively, the cover can comprise a material different than the walls. Whether or not a cover is present, the walls can have a height of at least 30 microns (i.e., the walls can rise above the base by at least 30 microns). For example, the walls can have a height of about 40 to about 100 microns.

In certain embodiments, the microfluidic circuit can include one or more (e.g., 2, 3, 4, 5, 6, 7, or more) microchannels. In addition, the microfluidic circuit can include a plurality of chambers (e.g., sequestration pens). The chambers can open off of one (or more) of the microchannels. In certain embodiments, the chamber can include a holding region configured to hold a liquid droplet, and at least one connection region that fluidically connects the holding region to a microfluidic channel. A first connection region can be configured to allow movement of the liquid droplet between the microfluidic channel and the chamber. A second connection region, if present, can be configured to allow for fluid flow and pressure relief when a liquid droplet is moved between the microfluidic channel and the holding region. In certain embodiments, the chamber can be connected to both a first microfluidic channel and a second microfluidic channel.

In certain embodiments, the microfluidic channel(s) can have a width of about 50 to about 1000 microns, or about 100 to about 500 microns, with the width measured in a direction normal to the direction of fluid flow through the channel. In certain embodiments, the chamber (or sequestration pen) can a cross-sectional area of about 100,000 to about 2,500,000 square microns, or about 200,000 to about 2,000,000 square microns. In certain embodiments, the connection region has a width of about 50 to about 500 microns, or about 100 to about 300 microns.

In certain embodiments, at least a portion of the base that helps to define the microchannel(s) and/or the chamber(s) can have a SSOEW configuration. The SSOEW configuration can be connected to a biasing potential and, while thus connected, change an effective wetting characteristic of any of a plurality of corresponding regions of the base surface. The wetting characteristic of the base surface can be changed sufficiently to move a liquid droplet across the substrate surface and between the microfluidic channel and the chamber.

In certain embodiments, the microfluidic device can include one or more culture chambers suitable for culturing biological micro-objects. The culture chamber(s) can be located within the microfluidic circuit, and each one can be fluidically connected to one or more microfluidic channels.

For example, a culture chamber can be fluidically connected to a first microfluidic channel which is configured for moving droplets to and/or from the culture chamber, and a second microfluidic channel that is configured to flow fresh culture medium past the culture chamber such that nutrients in the fresh culture medium and waste products in the culture chamber can be exchanged (e.g., by diffusion of nutrients into the culture chamber and diffusion of waste products out into the culture medium). The second channel can be separate from the first channel.

In another aspect, the invention provides methods for moving a droplet of fluid in a microfluidic device. The methods can include disposing a droplet of an aqueous solution on a top surface of a base of a microfluidic device, applying an AC voltage potential between a planar electrode and a mesh ground electrode of the microfluidic device, directing structured light at a position on the top surface of the base of the microfluidic device, in a location proximal to the droplet of aqueous solution, and moving the structured light relative to the microfluidic device at a rate that induces the droplet of aqueous solution to move across the top surface of the base. The microfluidic device can comprise a SSOEW-configured substrate, such as described herein.

In certain embodiments, the droplet of aqueous solution has a volume of about 1 microliter or less, about 900 nL or less, about 800 nL or less, about 700 nL or less, about 600 nL or less, about 500 nL or less, about 400 nL or less, about 300 nL or less, about 200 nL or less, about 100 nL or less, or about 50 nL or less. Alternatively, the droplet of aqueous solution can have a volume of greater than 1 microliter (e.g., at least about 1.1 microliters, at least about 1.2 microliters, at least about 1.3 microliters, at least about 1.4 microliters, at least about 1.5 microliters, at least about 1.6 microliters, at least about 1.7 microliters, at least about 1.8 microliters, at least about 1.9 microliters, at least about 2.0 microliters, at least about 2.2 microliters, at least about 2.4 microliters, at least about 2.6 microliters, at least about 2.8 microliters, at least about 3.0 microliters, or more). The droplet can have, for example, a conductivity of at least 0.1 mS/m (e.g., at least 1 mS/m). In certain embodiments, the AC voltage potential applied between the planar electrode and the mesh ground electrode of the microfluidic device is about 10 ppV to about 80 ppV (e.g., about 30 ppV to about 50 ppV). In certain embodiments, the AC voltage potential applied between the planar electrode and the mesh ground electrode of the microfluidic device has a frequency of about 1 kHz to about 1 MHz (e.g., about 1 kHz to about 100 kHz, about 2 kHz to about 80 kHz, about 3 kHz to about 60 kHz, about 4 kHz to about 40 kHz, or about 5 kHz to about 20 kHz). In certain embodiments, the structured light is moved relative to the microfluidic device at a rate of 0.05 cm/sec or greater (e.g., 0.1 cm/sec or greater, 0.2 cm/sec or greater, or 0.3 cm/sec or greater) and the droplet moves with the light.

In another aspect, the invention provides methods of processing droplets in a microfluidic device. The methods include filling a microfluidic circuit of a microfluidic device with a first liquid, applying an AC voltage potential between a planar electrode and a mesh ground electrode of the microfluidic device, introducing a first droplet of liquid medium into the microfluidic circuit, wherein the first droplet is immiscible in the first liquid medium, and moving the first droplet to a desired location within the microfluidic circuit by applying an electrowetting (EW) force to the first droplet. The microfluidic device can be any of the microfluidic devices described herein (e.g., a microfluidic device having a base that comprises a SSOEW-configured substrate). In addition, the microfluidic device comprises a droplet generator. The droplet generator can be configured to selectively provide droplets of one or more liquid media into the microfluidic circuit of the microfluidic device.

In certain embodiments, the applied AC voltage potential is about 10 ppV to about 80 ppV. For example, the applied AC voltage potential can be about 30 ppV to about 50 ppV. In addition, the applied AC voltage potential can have a frequency of about 1 to 100 kHz (e.g., about 1 kHz to about 100 kHz, about 2 kHz to about 80 kHz, about 3 kHz to about 60 kHz, about 4 kHz to about 40 kHz, or about 5 kHz to about 20 kHz).

In certain embodiments, the first liquid medium is an oil. For example, the first liquid medium is a silicone oil, a fluorinated oil, or a combination thereof. The first droplet can comprise an aqueous solution. The aqueous solution can be, for example, a saline solution or a cell culture medium.

In certain embodiments, the first droplet of liquid medium can comprise at least one micro-object. For example, the first droplet can comprise a biological micro-object (e.g., a single cell) or a capture bead (e.g., 1 to 20 capture beads). The capture bead can have an affinity for a material of interest, such as a biological cell secretion or a nucleic acid (e.g., DNA, genomic DNA, mitochondrial DNA, RNA, mRNA, miRNA, or any combination thereof).

In certain embodiments, the first droplet of liquid medium can comprise a reagent. The reagent can be a lysis buffer, a fluorescent label, a luminescent assay reagent, or the like. The lysis buffer can include a non-ionic detergent (e.g., at a concentration of less than 0.2%) or a proteolytic enzyme. The proteolytic enzyme can be inactivatable (e.g., by heat or specific inhibitor).

In certain embodiments, the methods of processing droplets in a microfluidic device further include: introducing a second droplet of liquid medium into the microfluidic circuit, wherein the liquid of the second droplet is immiscible in the first liquid medium but miscible with the liquid medium of the first droplet; moving the second droplet to a location within the microfluidic circuit adjacent to the first droplet by applying an EW force to the second droplet; and merging the second droplet with the first droplet to form a combined droplet. The second droplet can be merged with the first droplet by applying an EW force to the second and/or the first droplet.

In certain embodiments, the first droplet comprises a biological micro-object and the second droplet comprises a reagent. The reagent contained in the second droplet can be selected from the group consist of a lysis buffer, a fluorescent label, and a luminescent assay reagent. For example, the reagent contained in the second droplet can be a lysis buffer, and the biological micro-object (e.g., cell) in the first droplet can be lysed upon merger of the first droplet and the second droplet.

In some embodiments, the methods of processing droplets in a microfluidic device further include introducing third, fourth, etc. droplets into the microfluidic circuit and moving the third, fourth, etc. droplet to a desired location within the microfluidic circuit by applying an EW force to the droplet. The third droplet can be moved to a position proximal to the first combined droplet and then merged with the first combined droplet to form a second combined droplet; the fourth droplet can be moved to a position proximal to the second combined droplet and then merged with the second combined droplet to form a third combined droplet; and so on. Each additional droplet can contain a fluidic medium that is immiscible in the first liquid medium but miscible with the liquid medium of the first droplet (and/or first, second, etc. combined droplet).

In some embodiments, the first droplet can contain a biological cell and the second droplet can contain a reagent. The reagent can be a cell lysis buffer that lyses the biological cell when the first and second droplets are merged. Alternatively, the reagent can be a fluorescent label (e.g., a fluorescently-labeled antibody or other affinity reagent) or a reagent used in a luminescence assay. The third droplet can contain a reagent, such as one or more (e.g., two to twenty) capture beads having affinity for a material of interest. For example, the material of interest can be an antibody or a nucleic acid, such as DNA, genomic DNA, mitochondrial DNA, RNA, mRNA, miRNA, or any combination thereof. Such capture beads can optionally be exported from the apparatus for subsequent analysis. The fourth droplet can, like the second and third droplets, contain a reagent, such as an enzymatic mixture suitable for performing a reaction, such as a reverse transcriptase reaction or a whole genome amplification reaction.

In certain embodiments, applying an EW force to move and/or merge droplets comprises changing an effective electrowetting characteristic of a region of the top surface of the base of the microfluidic device proximal to the droplet(s). Changing the effective electrowetting characteristic can include activating EW electrodes (e.g., regions in the photoconductive layer) in the base of the microfluidic device at a location proximal to the droplet(s). Activating the EW electrodes in the base of the microfluidic device proximal to the droplet(s) can include directing a pattern of light onto the photoconductive layer of the base at the location proximal to the droplet(s).

Further aspects of the technology described herein will be brought out in the drawings and the following portions of the specification, wherein the detailed description is for the purpose of fully disclosing preferred embodiments of the technology without placing limitations thereon.

BRIEF DESCRIPTION OF THE DRAWINGS

FIG. 6A shows a cross-sectional view of the dielectric layer which has "T" shaped wires that make up the mesh electrode. FIG. 6B shows a top-down view of a mesh electrode that has square caps located at each vertex formed by the crossing of two wires. FIG. 6C shows a cross-sectional view of the dielectric layer in which the wires of the mesh electrode are supported by a dielectric material that is different from the dielectric material that flanks and covers the mesh electrode.

DETAILED DESCRIPTION OF THE INVENTION

Figure 1:
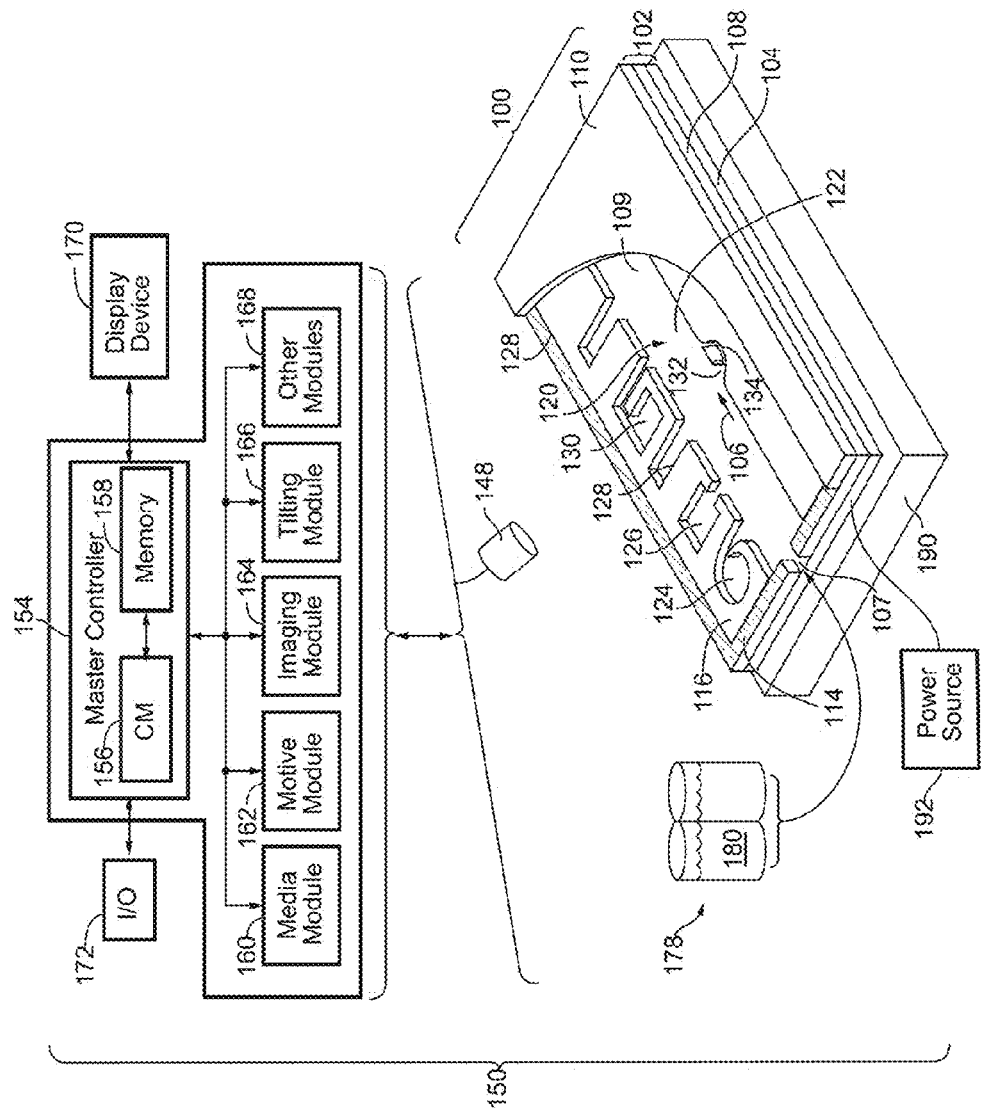
FIG. 1 illustrates an example of a system and associated control equipment for controlling a microfluidic device, which can be a single-sided opto-electrowetting (SSOEW) device.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s). Certain microfluidic devices (e.g., those that include a cover) will further include at least two ports configured to allow the fluid (and, optionally, micro-objects or droplets present in the fluid) to flow into and/or out of the microfluidic device. Some microfluidic circuits of a microfluidic device will include at least one microfluidic channel and/or at least one chamber. Some microfluidic circuits will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than the horizontal dimension (and vertical dimension, if the microfluidic device includes a cover). For example, the flow channel can be at least 5 times the length of either the horizontal (or vertical) dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and, if present, the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or between a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be manipulated in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cell, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices

FIG. 1 illustrates an example of a system 150 which can be used to control a microfluidic device 100, such as a SSOEW device, in the practice of the present invention. A perspective view of the microfluidic device 100 is shown having a partial cut-away of a cover 110 to provide a partial view into the microfluidic device 100. Of course, the cover 110 may not always be present, or may be present on part of the microfluidic device 100 but absent on another part of the microfluidic device 100. The microfluidic device 100 generally comprises a microfluidic circuit 120 comprising a flow path 106 through which a fluidic medium 180 can flow, optionally carrying one or more droplets (not shown) and/or one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic sequestration pens 124, 126, 128, and 130, each having one or more openings in fluidic communication with flow path 106. As discussed further below, the microfluidic sequestration pens comprise various features and structures that have been optimized for sequestering and separating droplets and/or micro-objects in the microfluidic device, such as microfluidic device 100, even when a medium 180 is flowing through the flow path 106.

As generally illustrated in FIG. 1, the microfluidic circuit 120 is defined by an enclosure 102. Enclosure 102 is depicted as comprising a support structure 104 (e.g., a base), a microfluidic circuit structure 108, and a cover 110. However, enclosure 102 can be physically structured in different configurations; as alluded to above, the microfluidic device 100 may lack a cover 110 over part or all of the support structure 104. Regardless, the support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120. Alternatively, if the microfluidic device lacks a cover 110, the microfluidic circuit structure 108 can be disposed on an inner surface 109 of the support structure 104, and together the support structure 104 and the microfluidic circuit structure 108 and can define the elements of the microfluidic circuit 120.

There can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110, if present. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to one or more electrodes (e.g., all or a subset of the semiconductor substrates can be electrically connected to a common electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with or otherwise contains fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110, if present, can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise the frame 114 and microfluidic circuit material 116 can be separate structures as shown in FIG. 1 or integral portions of the same structure.

In some embodiments, the cover 110, if present, can comprise a pierceable and/or deformable material. For example, the cover can comprise a flexible polymer, such as rubber, plastic, elastomer, silicone, polydimethylsiloxane ("PDMS"), or the like. In other embodiments, the cover 110 can comprise a rigid material. The rigid material may be glass or a material with similar properties. In some embodiments, the cover 110 can comprise both rigid and pierceable/deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110, or portions of it, can further include one or more electrodes. The one or more electrodes can comprise a conductive oxide, such as indium-tin-oxide (ITO), which may be coated on glass or a similarly rigid insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 further comprises a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100. The fluidic medium can be a hydrophobic medium, such as an oil (e.g., a silicone oil, a fluorinated oil, or a combination thereof), or a hydrophilic medium, such as a aqueous solution (e.g., a saline solution or a cell culture medium).

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107 or introduced directly into the enclosure 102). The media module 160 can also control removal of media from the enclosure 102 (e.g., through an outlet port (not shown) or direct removal). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to performing some other operation, such as using an opto-electrowetting force or other type of force (e.g., dielectrophoresis or gravity) to move a droplet and/or micro-object within the enclosure 102.

The motive module 162 can be configured to control selection, trapping, and movement of droplets and/or micro-objects (not shown) in the microfluidic circuit 120. As discussed below, the enclosure 102 can comprise an opto-electrowetting (OEW), dielectrophoresis (DEP), and/or optoelectronic tweezers (OET) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of droplets of medium, micro-objects, or the like). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate droplets and/or micro-objects inside the pen from fluidic medium 180, droplets, and/or micro-objects in the flow path 106 of channel 122 or in other pens. In some instances, pens 124, 126, 128, 130 are configured to physically corral one or more droplets and/or micro-objects within the microfluidic circuit 120. Sequestration pens in accordance with the present invention can comprise various shapes, surfaces and features that are optimized for use with OEW, DEP, OET, and/or gravitational forces, as will be discussed below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for the manipulation of droplets and/or micro-objects. In some embodiments, the microfluidic circuit 120 comprises a plurality of identical microfluidic sequestration pens. In some embodiments, the microfluidic circuit 120 comprises a plurality of microfluidic sequestration pens, wherein two or more of the sequestration pens comprise differing structures and/or features which provide differing benefits. For example, microfluidic sequestration pens in accordance with the present invention may be configured to isolate droplets for processing cells (e.g., for nucleic acid extraction and/or processing), isolated cells for cell culture, and/or isolate cellular components, such as nucleic acids, proteins, or metabolites, for processing and/or amplification.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens are configured (e.g., relative to a channel 122) such that they can be loaded with droplets and/or target micro-objects (e.g., cells) in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single droplet or micro-object from the flow path 106. In some embodiments, the traps 132 are configured to receive or capture a plurality of droplets or micro-objects from the flow path 106. In some instances, the traps 132 comprise a volume approximately equal to the volume of a single droplet or target micro-object.

The traps 132 may further comprise an opening 183 which is configured to assist the flow of droplets or targeted micro-objects into the traps 132. In some instances, the traps 132 comprise an opening having a width (and, optionally, a height) that is approximately equal to the dimensions of a single target micro-object, whereby larger droplets or micro-objects are prevented from entering into the micro-object trap. The traps 132 may further comprise other features configured to assist in retention of droplets or targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped droplet or micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the teachings of the instant invention.

In other embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the instant invention. In some embodiments, the DEP forces comprise optoelectronic tweezer (OET) forces.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

A variety of optically-actuated electrokinetic devices are known in the art, including devices having an optoelectronic tweezer (OET) configuration and devices having an optoelectrowetting (OEW) configuration. Examples of OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Figure 2A:
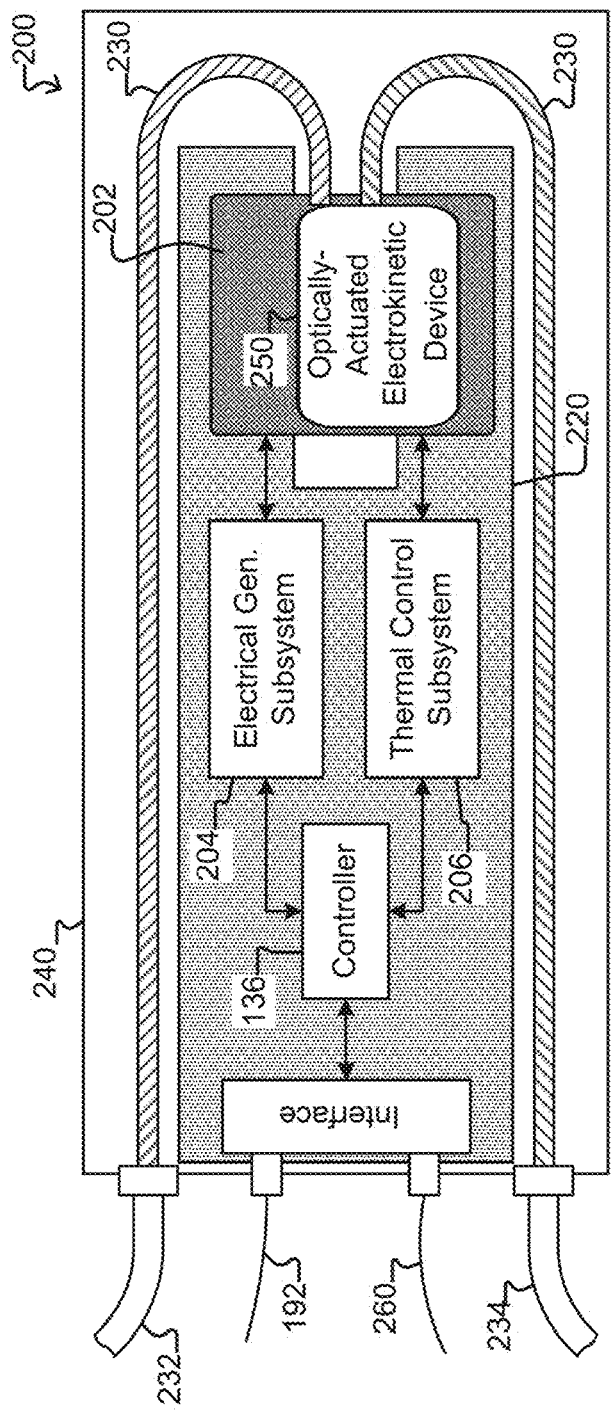
FIG. 2A illustrates a specific example of a support which can be part of the system and can be configured to hold and operatively couple with a microfluidic device.

FIGS. 2A through 2D show various embodiments of system 150 which can be used to operate and observe microfluidic devices (e.g. 100) according to the present invention. As illustrated in FIG. 2A, the system 150 can include a structure ("nest") 200 configured to hold and operatively couple with a microfluidic device 250, which can be a microfluidic device described herein. The nest 200 can include a socket 202 capable of interfacing with the microfluidic device 250 (e.g., an optically-actuated electrokinetic device, such as a microfluidic device having a SSOEW configuration) and providing electrical connections from power source 192 to microfluidic device 250. The nest 200 can further include an integrated electrical signal generation subsystem 204. The electrical signal generation subsystem 204 can be configured to supply a biasing voltage to socket 202 such that the biasing voltage is applied across a pair of electrodes in the microfluidic device 250 when it is being held by socket 202. Thus, the electrical signal generation subsystem 204 can be part of power source 192. The ability to apply a biasing voltage to microfluidic device 250 does not mean that a biasing voltage will be applied at all times when the microfluidic device 250 is held by the socket 202. Rather, in most cases, the biasing voltage will be applied intermittently, e.g., only as needed to facilitate the generation of electrokinetic forces, such as electro-wetting or dielectrophoresis, in the microfluidic device 250.

As illustrated in FIG. 2A, the nest 200 can include a printed circuit board assembly (PCBA) 220. The electrical signal generation subsystem 204 can be mounted on and electrically integrated into the PCBA 220. The exemplary support includes socket 202 mounted on PCBA 320, as well.

Typically, the electrical signal generation subsystem 204 will include a waveform generator (not shown). The electrical signal generation subsystem 204 can further include an oscilloscope (not shown) and/or a waveform amplification circuit (not shown) configured to amplify a waveform received from the waveform generator. The oscilloscope, if present, can be configured to measure the waveform supplied to the microfluidic device 250 held by the socket 202. In certain embodiments, the oscilloscope measures the waveform at a location proximal to the microfluidic device 250 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 200 further comprises a controller 208, such as a microprocessor used to sense and/or control the electrical signal generation subsystem 204. Examples of suitable microprocessors include the Arduino™ microprocessors, such as the Arduino Nano™. The controller 208 may be used to perform functions and analysis or may communicate with an external master controller 154 (shown in FIG. 1) to perform functions and analysis. In the embodiment illustrated in FIG. 2A the controller 208 communicates with a master controller 154 through an interface 210 (e.g., a plug or connector).

In some embodiments, the nest 200 can comprise an electrical signal generation subsystem 204 comprising a Red Pitaya™ waveform generator/oscilloscope unit ("Red Pitaya™ unit") and a waveform amplification circuit that amplifies the waveform generated by the Red Pitaya™ unit and passes the amplified voltage to the microfluidic device 100. In some embodiments, the Red Pitaya™ unit is configured to measure the amplified voltage at the microfluidic device 250 and then adjust its own output voltage as needed such that the measured voltage at the microfluidic device 250 is the desired value. In some embodiments, the waveform amplification circuit can have a +6.5V to −6.5V power supply generated by a pair of DC-DC converters mounted on the PCBA 220, resulting in a signal of up to 13 Vpp at the microfluidic device 250.

As illustrated in FIG. 2A, the nest 200 can further include a thermal control subsystem 206. The thermal control subsystem 206 can be configured to regulate the temperature of microfluidic device 250 held by the nest 200. For example, the thermal control subsystem 206 can include a Peltier thermoelectric device (not shown) and a cooling unit (not shown). The Peltier thermoelectric device can have a first surface configured to interface with at least one surface of the microfluidic device 250. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 230 configured to circulate cooled fluid through the cooling block. In the embodiment illustrated in FIG. 2A, the nest 200 comprises an inlet 232 and an outlet 234 to receive cooled fluid from an external reservoir (not shown), introduce the cooled fluid into the fluidic path 230 and through the cooling block, and then return the cooled fluid to the external reservoir. In some embodiments, the Peltier thermoelectric device, the cooling unit, and/or the fluidic path 230 can be mounted on a casing 240 of the nest 200. In some embodiments, the thermal control subsystem 206 is configured to regulate the temperature of the Peltier thermoelectric device so as to achieve a target temperature for the microfluidic device 250. Temperature regulation of the Peltier thermoelectric device can be achieved, for example, by a thermoelectric power supply, such as a Pololu™ thermoelectric power supply (Pololu Robotics and Electronics Corp.). The thermal control subsystem 206 can include a feedback circuit, such as a temperature value provided by an analog circuit. Alternatively, the feedback circuit can be provided by a digital circuit.

In some embodiments, the nest 200 can include a thermal control subsystem 206 with a feedback circuit that is an analog voltage divider circuit which includes a resistor (e.g., with resistance 1 kOhm+/−0.1%, temperature coefficient+/−0.02 ppm/C0) and a NTC thermistor (e.g., with nominal resistance 1 kOhm+/−0.01%). In some instances, the thermal control subsystem 206 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 200 can include a serial port 260 which allows the microprocessor of the controller 208 to communicate with an external master controller 154 via the interface 210. In addition, the microprocessor of the controller 208 can communicate (e.g., via a Plink tool (not shown)) with the electrical signal generation subsystem 204 and thermal control subsystem 206. Thus, via the combination of the controller 208, the interface 210, and the serial port 260, the electrical signal generation subsystem 208 and the thermal control subsystem 206 can communicate with the external master controller 154. In this manner, the master controller 154 can, among other things, assist the electrical signal generation subsystem 208 by performing scaling calculations for output voltage adjustments. A Graphical User Interface (GUI) provided via a display device 170 coupled to the external master controller 154, can be configured to plot temperature and waveform data obtained from the thermal control subsystem 206 and the electrical signal generation subsystem 208, respectively. Alternatively, or in addition, the GUI can allow for updates to the controller 208, the thermal control subsystem 206, and the electrical signal generation subsystem 204.

As discussed above, system 150 can include an imaging device 194. In some embodiments, the imaging device 194 comprises a light modulating subsystem 304. The light modulating subsystem 304 can include a digital mirror device (DMD) or a microshutter array system (MSA), either of which can be configured to receive light from a light source 302 and transmits a subset of the received light into an optical train of microscope 300. Alternatively, the light modulating subsystem 304 can include a device that produces its own light (and thus dispenses with the need for a light source 302), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 304 can be, for example, a projector. Thus, the light modulating subsystem 304 can be capable of emitting both structured and unstructured light. One example of a suitable light modulating subsystem 304 is the Mosaic™ system from Andor Technologies™. In certain embodiments, imaging module 164 and/or motive module 162 of system 150 can control the light modulating subsystem 304.

In certain embodiments, the imaging device 194 further comprises a microscope 300. In such embodiments, the nest 200 and light modulating subsystem 304 can be individually configured to be mounted on the microscope 300. The microscope 300 can be, for example, a light microscope or fluorescence microscope. Thus, the nest 200 can be configured to be mounted on the stage 310 of the microscope 300 and/or the light modulating subsystem 304 can be configured to mount on a port of microscope 300. In other embodiments, the nest 200 and the light modulating subsystem 304 described herein can be integral components of microscope 300.

In certain embodiments, the microscope 300 can further include one or more detectors 322. In some embodiments, the detector 422 is controlled by the imaging module 164. The detector 322 can include an eye piece, a charge-coupled device (CCD), a camera (e.g., a digital camera), or any combination thereof. If at least two detectors 322 are present, one detector can be, for example, a fast-frame-rate camera while the other detector can be a high sensitivity camera. Furthermore, the microscope 300 can include an optical train configured to receive reflected and/or emitted light from the microfluidic device 250 and focus at least a portion of the reflected and/or emitted light on the one or more detectors 322. The optical train of the microscope can also include different tube lenses (not shown) for the different detectors, such that the final magnification on each detector can be different.

In certain embodiments, imaging device 194 is configured to use at least two light sources. For example, a first light source 302 can be used to produce structured light (e.g., via the light modulating subsystem 304) and a second light source 332 can be used to provide unstructured light. The first light source 302 can produce structured light for optically-actuated electrokinesis and/or fluorescent excitation, and the second light source 332 can be used to provide bright field illumination. In these embodiments, the motive module 162 can be used to control the first light source 304 and the imaging module 164 can be used to control the second light source 332. The optical train of the microscope 300 can be configured to (1) receive structured light from the light modulating subsystem 304 and focus the structured light on at least a first region in a microfluidic device, such as an optically-actuated electrokinetic device (e.g., a microfluidic device having a SSOEW configuration), when the device is being held by the nest 200, and (2) receive reflected and/or emitted light from the microfluidic device and focus at least a portion of such reflected and/or emitted light onto detector 322. The optical train can be further configured to receive unstructured light from a second light source and focus the unstructured light on at least a second region of the microfluidic device, when the device is held by the nest 200. In certain embodiments, the first and second regions of the microfluidic device can be overlapping regions. For example, the first region can be a subset of the second region.

Figure 2B:
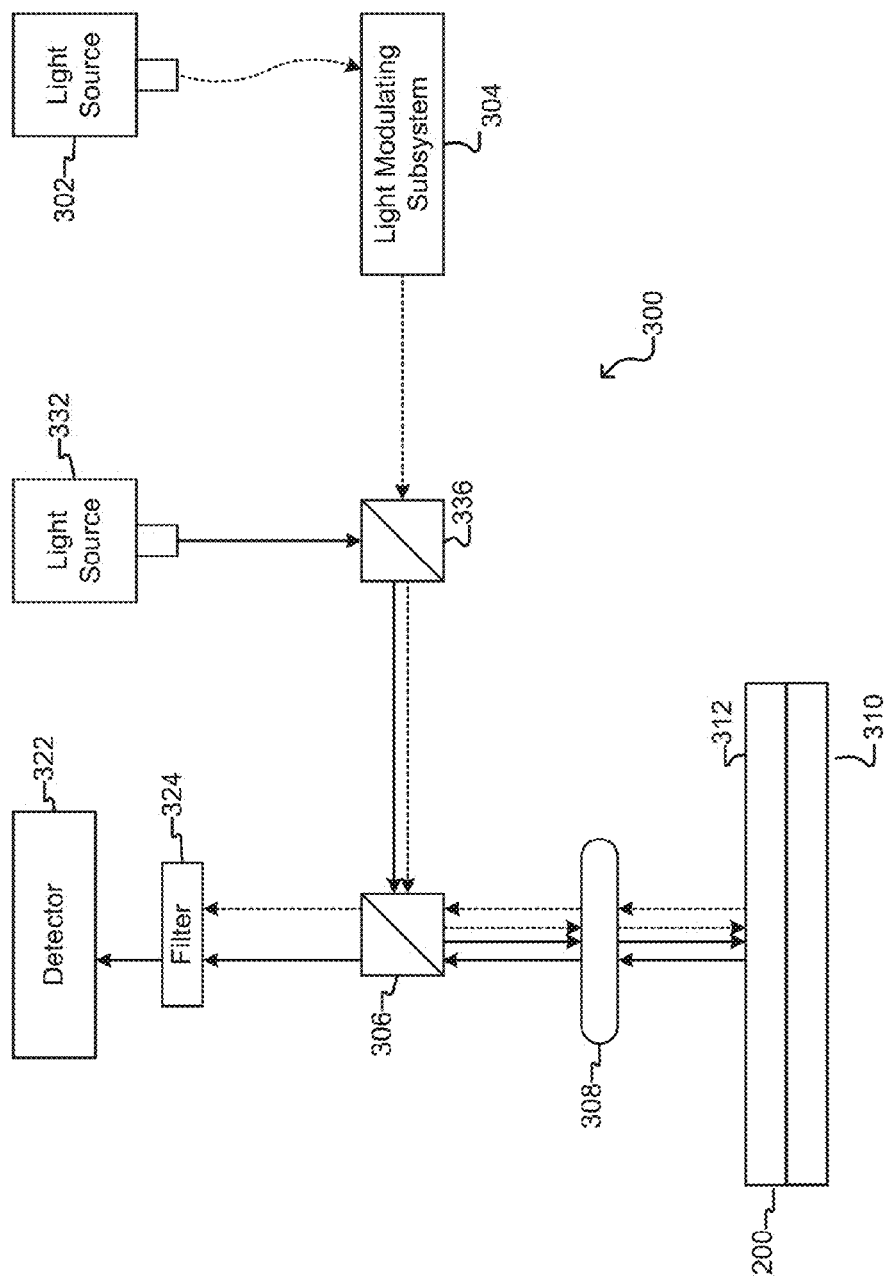
FIG. 2B illustrates an imaging device which can be part of the system.

In FIG. 2B, the first light source 302 is shown supplying light to a light modulating subsystem 304, which provides structured light to the optical train of the microscope 300. The second light source 332 is shown providing unstructured light to the optical train via a beam splitter 336. Structured light from the light modulating subsystem 304 and unstructured light from the second light source 332 travel from the beam splitter 336 through the optical train together to reach a second beam splitter 336 (or dichroic filter 306 depending on the light provided by the light modulating subsystem 304), where the light gets reflected down through the objective 308 to the sample plane 312. Reflected and/or emitted light from the sample plane 312 then travels back up through the objective 308, through the beam splitter/dichroic filter 306, and to a dichroic filter 324. Only a fraction of the light reaching dichroic filter 324 passes through and reaches the detector 322.

In some embodiments, the second light source 332 emits blue light. With an appropriate dichroic filter 324, blue light reflected from the sample plane 312 is able to pass through dichroic filter 324 and reach the detector 322. In contrast, structured light coming from the light modulating subsystem 304 gets reflected from the sample plane 312, but does not pass through the dichroic filter 324. In this example, the dichroic filter 324 is filtering out visible light having a wavelength longer than 495 nm. Such filtering out of the light from the light modulating subsystem 304 would only be complete (as shown) if the light emitted from the light modulating subsystem did not include any wavelengths shorter than 495 nm. In practice, if the light coming from the light modulating subsystem 304 includes wavelengths shorter than 495 nm (e.g., blue wavelengths), then some of the light from the light modulating subsystem would pass through filter 324 to reach the detector 322. In such an embodiment, the filter 324 acts to change the balance between the amount of light that reaches the detector 322 from the first light source 302 and the second light source 332. This can be beneficial if the first light source 302 is significantly stronger than the second light source 332. In other embodiments, the second light source 332 can emit red light, and the dichroic filter 324 can filter out visible light other than red light (e.g., visible light having a wavelength shorter than 650 nm).

Substrates Having a Single-Sided Optoelectrowetting (SSOEW) Configuration.

Figure 3A:
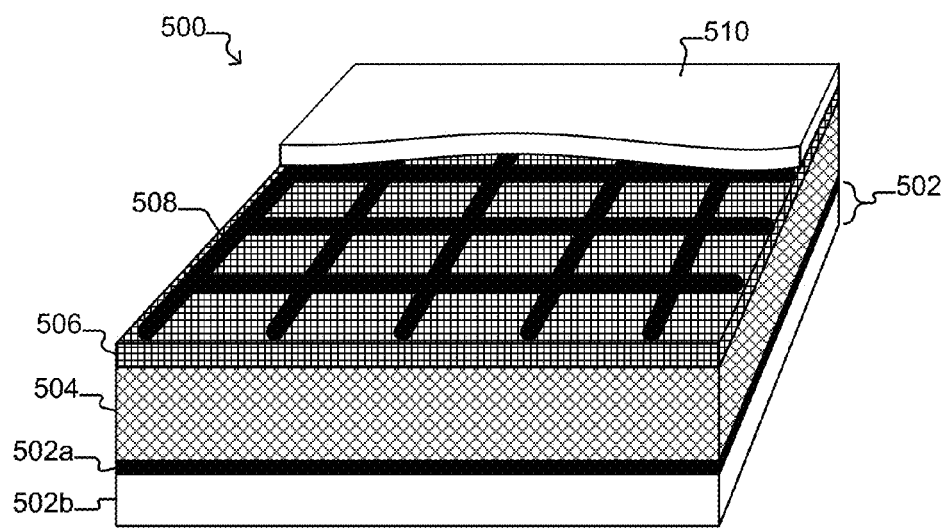
FIGS. 3A and 3B illustrate a cut-away view (FIG. 3A) and a cross-sectional view (FIG. 3B) of a portion of a SSOEW device according to one embodiment of the invention.
Figure 3B:
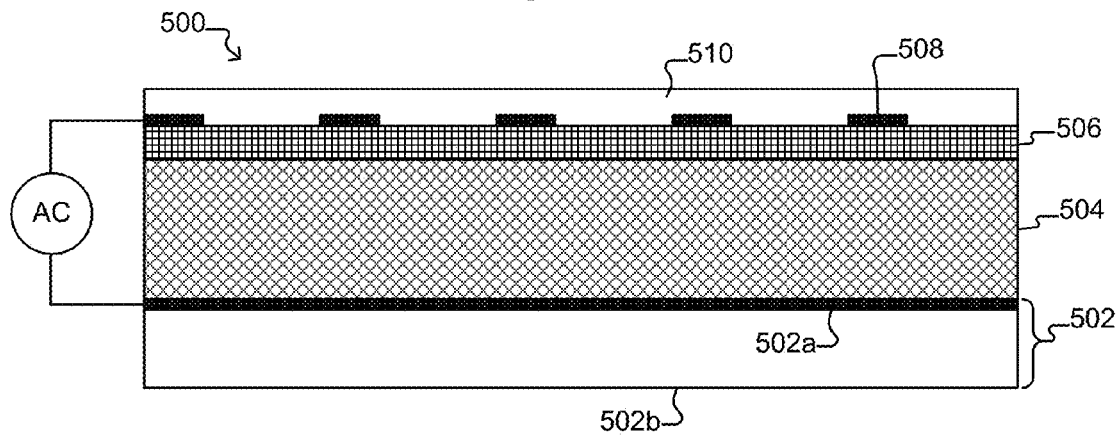

In some embodiments, a SSOEW substrate of the invention can include a planar electrode, a photoconductive (or photosensitive) layer, a dielectric layer, a mesh electrode, and a hydrophobic coating. An example of a SSOEW substrate 500 of the invention is shown in FIGS. 3A-B. The photoconductive layer 504 can be interposed between the planar electrode 502 and the dielectric layer 506; and the mesh electrode 508 can adjoin a top surface of the dielectric layer (i.e., the surface opposite to the side that contacts the photoconductive layer). The insulating coating 510 can cover the dielectric layer 506, as well as any part of the mesh electrode 508 that is not embedded in the dielectric layer 506.

The dielectric layer 506 can be a single layer, as depicted in FIGS. 3A-B, and can comprise, consist essentially of, or consist of an oxide. The oxide can have a dielectric constant of about 5 to about 15 (e.g., about 7.5 to about 12.5, or about 9 to about 11.5). As an example, the oxide can be a metal oxide, such as aluminum oxide or hafnium oxide. The dielectric layer 506 can be formed, for example, by atomic layer deposition (ALD). Use of ALD for the formation of the dielectric layer 506 (or portions thereof, as discussed further below) can be advantageous because it deposits conformal films, with well-controlled thickness, that are substantially pinhole free (i.e., there are few to none electrical shorts through the dielectric layer).

Figure 5A:
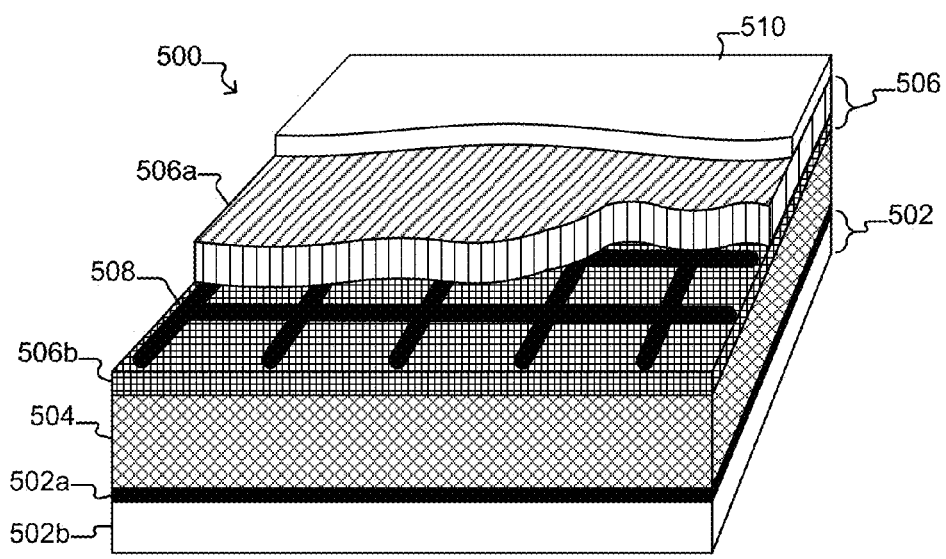
FIGS. 5A and 5B illustrate a cut-away view (FIG. 5A) and a cross-sectional view (FIG. 5B) of a portion of a single-sided OEW device according to one embodiment of the invention.
Figure 5B:
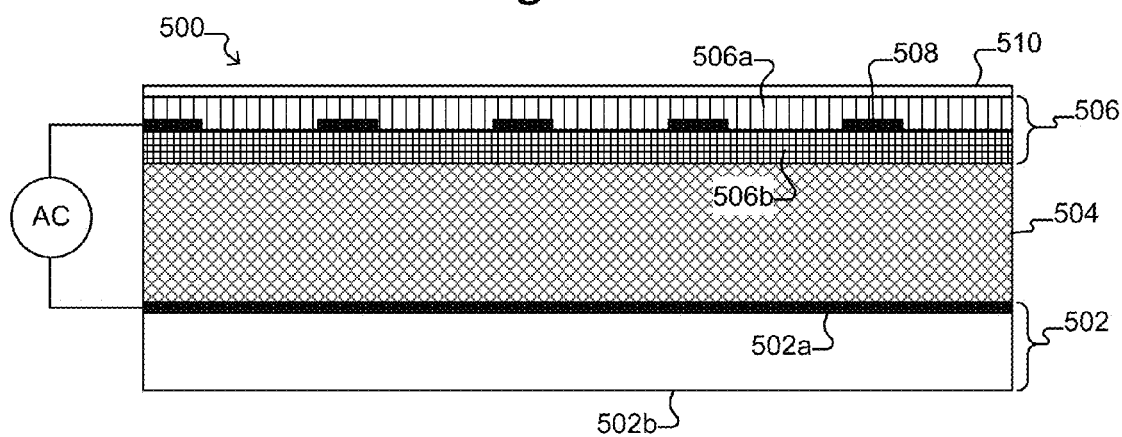

Alternatively, the dielectric layer 506 can have a multilayer (or "composite") structure that includes 2, 3, or more layers, each of which comprises a dielectric material. For example, as shown in FIGS. 5A-B and 6C, the dielectric layer 506 can have a first dielectric layer 506a and a second dielectric layer 506b, with the bottom surface of the first dielectric layer 506a adjoining the photoconductive layer 504. The mesh electrode can be interposed between the first dielectric layer 506a and the second dielectric layer 506b of a two-layer composite dielectric layer 506, as shown. However, this is not a requirement, as the mesh electrode can rest upon (e.g., be adjacent to) the top surface of the second dielectric layer 506b.

The first dielectric layer 506a and second dielectric layer 506b of a two-layer composite dielectric layer 506 can include similar or substantially identical dielectric materials. For example, both the first dielectric layer 506a and the second dielectric layer 506b can comprise a metal oxide, such as aluminum oxide or hafnium oxide. In addition, one or both of the first dielectric layer 506a and the second dielectric layer 506b can be formed by ALD. When the composite dielectric layer 506 is configured in this manner, the first dielectric layer 506a can be a larger (e.g., thicker) component of the composite dielectric layer 506. For example, the first dielectric layer 506a can have a thickness of at least about 100 nm, at least about 125 nm, at least about 150 nm, or more (or about 125 nm to about 175 nm, or about 140 nm to about 160 nm), and the second dielectric layer 506b can have a thickness of about 50 nm or less (e.g., about 40 nm or less, about 30 nm or less, about 25 nm or less, about 20 nm or less, about 15 nm or less, about 10 nm or less, about 9 nm or less, about 8 nm or less, about 7 nm or less, about 6 nm or less, about 5 nm or less, about 4 nm or less, or about 3 nm or less). In particular, the first dielectric layer 506a can have a thickness of at least about 125 nm (e.g., at least about 150 nm) and the second dielectric layer 506b can have a thickness of about 10 nm or less (e.g., about 5 nm or less).

The first dielectric layer 506a of a composite dielectric layer 506 can have a lattice shape, as shown in FIG. 6C (in cross-section). The lattice can be of substantially uniform thickness, with the top surface of the first dielectric layer 506a adjoining a bottom surface of the mesh electrode 508 and the mesh electrode 508 interposed between the first dielectric layer 506a and the second dielectric layer 506b. The top surface of the first dielectric layer 506a can be substantially contiguous with the bottom surface of the mesh electrode 508 (i.e., the width of individual linear elements of the lattice of the first dielectric layer 506a can be substantially equal to the width of individual wires in the mesh electrode, as shown in FIG. 6C). Configured in this manner, the first dielectric layer 506a and the second dielectric layer 506b of the composite dielectric layer 506 can include different dielectric materials. For example, the first dielectric layer 506a can include a metal oxide, such as aluminum oxide or hafnium oxide, and the second dielectric layer 506b can include a non-metal oxide, such as silicon oxide. The thickness of the first dielectric layer 506a can be at least about 50 nm, at least about 75 nm, at least about 100 nm, at least about 125 nm, at least about 150 nm, or more. For example, the first dielectric layer 506a can have a thickness of about 50 nm to about 200 nm, about 75 nm to about 180 nm, about 100 nm to about 160 nm, or about 125 nm to about 150 nm. And the thickness of the second dielectric layer 506b can be variable. For example, the second dielectric layer 506b can have first regions contacting the top surface of the photoconductive layer 504 with a thickness substantially the same as the thickness of the composite dielectric layer 506, and second regions directly over the wires of the mesh electrode 508 having a thickness of about 100 nm or less (e.g., about 75 nm or less, about 50 nm or less, about 40 nm or less, about 30 nm or less, about 25 nm or less, about 20 nm or less, about 15 nm or less, about 10 nm or less, about 9 nm or less, about 8 nm or less, about 7 nm or less, about 6 nm or less, about 5 nm or less, about 4 nm or less, or about 3 nm or less). In particular, the first dielectric layer 506a can include a metal oxide and have a thickness of at least about 125 nm (e.g., at least about 150 nm), and the second dielectric layer 506b can include a non-metal oxide and have a thickness directly over the wires of the mesh electrode 508 of about 10 nm or less (e.g., about 5 nm or less).

The first dielectric layer 506a of a composite dielectric layer 506 can comprise, consist essentially of, or consist of a first material having a dielectric constant $\in_1$, and the second dielectric layer 506b can comprise, consist essentially of, or consist of a second material having a dielectric constant $\in_2$, where $\in_1$ is different than $\in_2$ (e.g., $\in_1$ can be less than $\in_2$). For example, the first material can be a metal oxide, such as aluminum oxide or hafnium oxide, and the second material can be a non-metal oxide, such as silicon oxide.

Figure 6A:
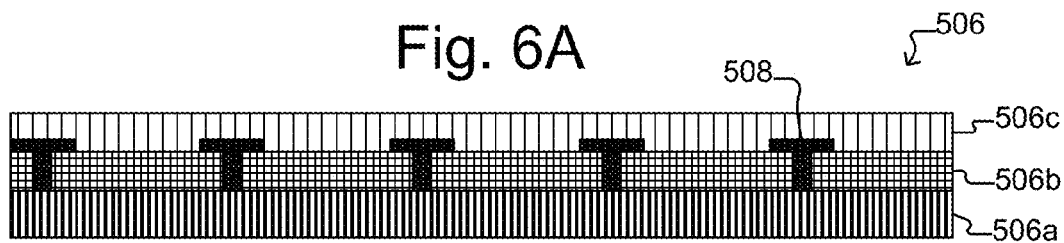
FIGS. 6A-6C illustrate alternative embodiments for a mesh electrode-containing dielectric layer of the SSOEW device of FIGS. 5A and 5B.

As shown in FIG. 6A, a composite dielectric layer 506 can have a first dielectric layer 506a, a second dielectric layer 506b, and a third dielectric layer 506c, with the bottom surface of the first dielectric layer 506a adjoining the photoconductive layer 504 and the second dielectric layer 506b interposed between the first dielectric layer 506a and the third dielectric layer 506c. Configured in this manner, the first dielectric layer 506a and the third dielectric layer 506c can include similar or substantially identical dielectric materials. For example, the first dielectric layer 506a and the third dielectric layer 506c can each comprise, consist essentially of, or consist of a metal oxide (e.g., aluminum oxide or hafnium oxide). In addition, the first dielectric layer 506a and the third dielectric layer 506c can be formed, for example, by ALD. Alternatively, the first dielectric layer 506a and the third dielectric layer 506c can include different dielectric materials and/or can be formed by different processes.

The second dielectric layer 506b of a three-layer composite dielectric layer 506 can include a dielectric material that is different from that of the first dielectric layer 506a and/or the third dielectric layer 506c. The second dielectric layer 506b can comprise, consist essentially of, or consist of, for example, a non-metal oxide, such as silicon oxide, or a nitride. In addition, the second dielectric layer 506b can be formed in a manner different from that of the first dielectric layer 506a and/or the third dielectric layer 506c. For example, the second dielectric layer 506b can be formed by plasma enhanced chemical vapor deposition.

For a three-layer composite dielectric layer 506, each of the first dielectric layer 506a and the third dielectric layer 506c can have a thickness of at least about 5 nm (e.g., about 6 nm to about 12 nm, about 7 nm to about 14 nm, about 8 nm to about 16 nm, about 9 nm to about 18 nm, or about 10 nm to about 20 nm). The second dielectric layer 506b can have a thickness of at least about 75 nm (e.g., about 100 nm to about 300 nm, about 110 nm to about 275 nm, about 120 nm to about 250 nm, about 130 nm to about 225 nm, or about 140 nm to about 200 nm).

The first dielectric layer 506a of a three-layer composite dielectric layer 506 can have a top surface adjoining a bottom surface of the mesh electrode 508, and the third dielectric layer 506c can have a bottom surface adjoining a top surface of the mesh electrode 508. Thus, for example, the mesh ground electrode can be entirely encased within the composite dielectric layer, with the second dielectric layer 506b filling the spaces formed between the lateral edges of the wires of the mesh ground electrode. Alternatively, the mesh electrode 508 can rest upon (e.g., be adjacent to) the top surface of the third dielectric layer 506c.

The first dielectric layer 506a of a three-layer composite dielectric layer 506 can be made from a first material that has a dielectric constant the second dielectric layer 506b can be made from a second material that has a dielectric constant $\in_2$, and the third dielectric layer 506c can be made from a third material that has a dielectric constant $\in_3$. Depending on the configuration of the mesh electrode 508 relative to the layers of the composite dielectric layer 506, $\in_1$ can be different than $\in_3$. For example, $\in_1$ can be similar to or substantially the same as $\in_3$, and $\in_2$ can be greater than $\in_1$ and $\in_3$. Alternatively, $\in_1$ can be less than $\in_3$, and $\in_2$ can be less than $\in_3$ (e.g., $\in_2$ can have a value equal to or greater than $\in_1$ but less than $\in_3$).

A single-layer dielectric layer 506 can have a thickness of at least 50 nm, at least about 75 nm, at least about 100 nm, at least about 125 nm, at least about 150 nm, or more. Thus, the dielectric layer 506 can have a thickness ranging from about 50 to about 250 nm, about 75 nm to about 225 nm, about 100 nm to about 200 nm, about 125 nm to about 175 nm, or about 140 nm to about 160 nm. Similarly, a composite dielectric layer (two-layer, three-layer, or more) can have an overall thickness of at least about 50 nm, at least about 75 nm, at least about 100 nm, at least about 125 nm, at least about 150 nm, or more. For example, the composite dielectric layer can have an overall thickness of about 50 to about 250 nm, about 75 nm to about 225 nm, about 100 nm to about 200 nm, about 125 nm to about 175 nm, or about 140 nm to 160 nm.

As one skilled in the art will understand, the number of layers in the dielectric layer 506 and the overall thickness of the dielectric layer 506 can be varied, depending upon other elements and design features of the SSOEW-configured substrate 500, such that the electrical impedance of the dielectric layer 506 is suitable for achieving the desired effect—an SSOEW-configured substrate that can reliably and controllably produce an EW force. Generally, the dielectric layer 506 (whether single-layer or multi-layer) will have an electrical impedance of about 10 kOhms to about 50 kOhms, or about 10 kOhms to about 20 kOhms. For example, the dielectric layer 506 can have an overall thickness of at least 125 nm (e.g., at least 150 nm), inclusive of all of the one or more dielectric layers (e.g., 506a, 506b, 506c, etc.), and an electrical impedance of about 10 kOhms to about 50 kOhms (e.g., about 10 kOhms to about 20 kOhms).

Figure 6B:
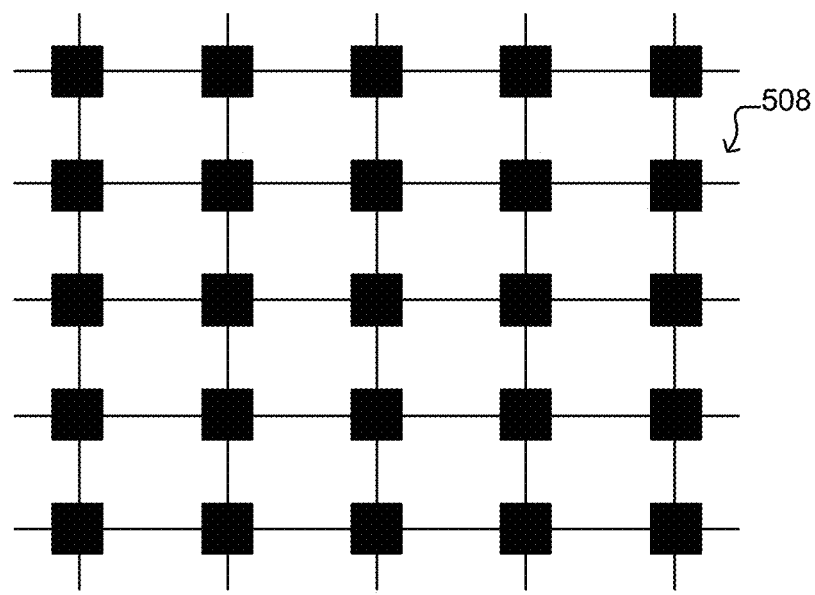
Figure 6C:
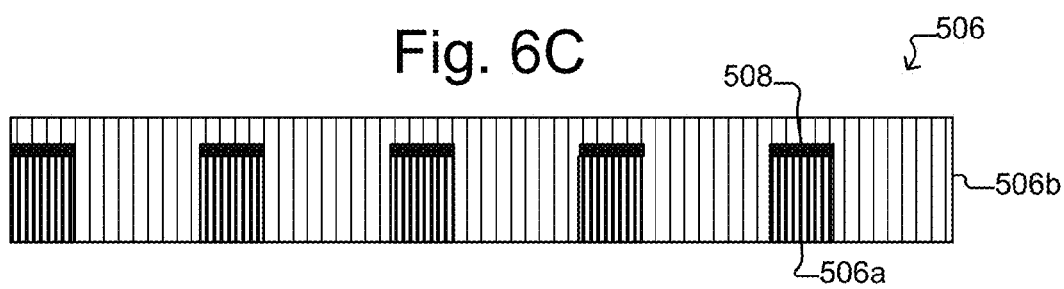

As illustrated in FIGS. 3A and 5A, the mesh electrode 508 can comprise a plurality of wires arranged in a lattice shape. The wires of the mesh electrode 508 can have a substantially square shape or a substantially rectangular shape, when viewed in cross-section (see FIGS. 3B, 4A, 5B, and 6C). Thus, the wires can have an average width and an average height. The average height of the wires can be at least about 50 nm, at least about 60 nm, at least about 70 nm, at least about 80 nm, at least about 90 nm, or at least about 100 nm. The average width of the wires can be at least about 100 nm, at least about 200 nm, at least about 300 nm, at least about 400 nm, at least about 500 nm, at least about 600 nm, at least about 700 nm, at least about 800 nm, at least about 900 nm, or at least about 1000 nm. However, other shapes are also possible and have the potential to improve the performance of the SSOEW-configured substrate 500. For example, the wires of the mesh electrode 508 can have a T-shape when viewed in cross section (see FIG. 6A). In addition, the mesh electrode 508 can further comprise plates located on top of the vertices formed by the wires of the mesh electrode 508 (see FIG. 6B). The plates can have substantially the same composition as the wires of the mesh ground electrode 508. The wires of the mesh electrode 508 can be directly deposited on the dielectric layer 506 (or a first dielectric layer 506a, a second dielectric layer 506b, or a third dielectric layer 506c, etc., of a composite dielectric layer 506), and can be of substantially uniform thickness.

The wires of the mesh electrode 508 can comprise (or consist essentially of, or consist of) a conductive material, such as a metal, a metal alloy, or a highly electrically conductive semiconductor material. For example, the wires of the mesh electrode 508 can comprise gold, aluminum, titanium, chromium, combinations thereof, and/or oxidized variants thereof. In particular, if the wires of the mesh electrode comprise gold, they can include a layer of chromium or titanium (e.g., to help bind the gold to the underlying dielectric layer 506). Alternatively, the wires of the mesh electrode 508 can comprise highly-doped silicon. Optionally, the conductive material used in the mesh electrode 508 can be non-toxic to biological (e.g., animalian, mammalian, or human) cells.

The mesh electrode 508 can have a linear fill factor β that is less than or equal to about 10% (e.g., less than about 9%, less than about 8%, less than about 7%, less than about 6%, less than about 5%, less than about 4%, less than about 3%, less than about 2%, less than about 1%, or less than about 0.5%). The wires of the mesh electrode 508 can have a pitch of less than 1 mm. For example, the wires of the mesh ground electrode 508 can have a pitch of about 1.5 mm to about 2 mm, about 1.0 mm to about 1.5 mm, about 0.5 mm to about 1.0 mm, about 400 to about 800 microns, about 300 to about 600 microns, about 200 to about 400 microns, about 100 to about 200 microns, about 50 to about 100 microns, or about 10 to about 50 microns. As discussed further below, the pitch of the wires can be adjusted depending on the size of the droplets that will be moved upon the SSOEW-configured substrate 500.

Figure 4A:
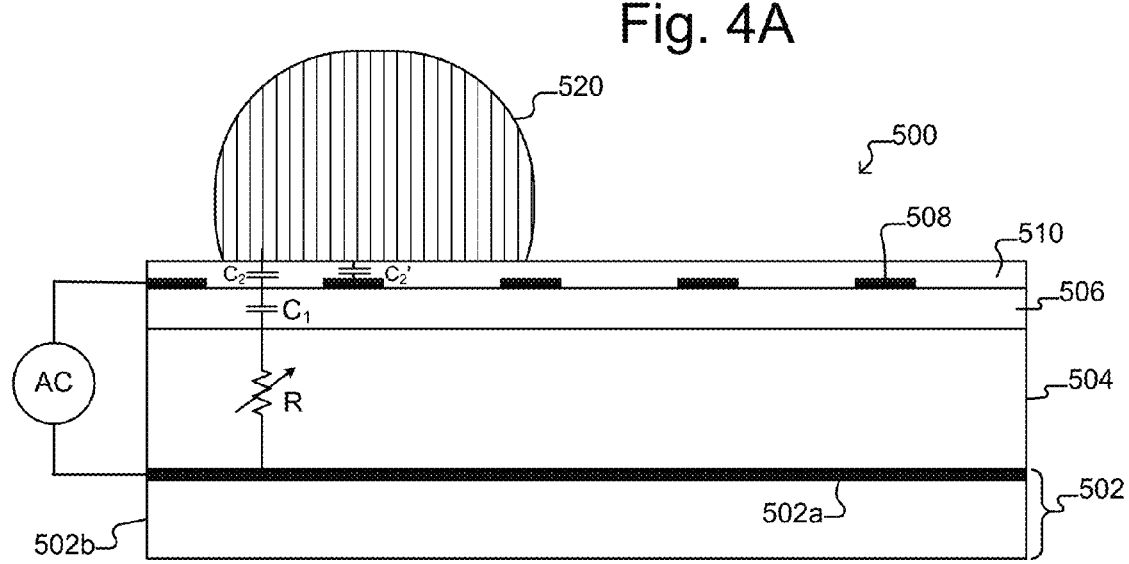
FIG. 4A illustrates the SSOEW device of FIG. 3B overlaid with an electrical circuit diagram showing resistive and capacitive elements of the SSOEW device when an aqueous droplet is positioned on the surface of the device and a voltage source is placed between a bottom electrode and an upper mesh electrode.

As illustrated in FIGS. 3A-B, 4A, 5A-B, 6A, and 6C, the hydrophobic coating 510 of a SSOEW-configured substrate 500 has a bottom surface that adjoins some or all of the top surface of the dielectric layer 506. Provided that the mesh electrode 508 rests on top of the dielectric layer 506, and is not embedded in the dielectric layer 506 (e.g., as shown in FIGS. 3A-B and 4A), the bottom surface of the hydrophobic coating 510 will also adjoin the top surfaces (and possibly the lateral surfaces) of the wires of the mesh electrode 508. To achieve appropriate bonding between the hydrophobic coating 510 and exposed surfaces on the wires of the mesh electrode 508, the exposed surfaces of the wires may require conditioning. For example, gold tends to bond poorly to the molecules of the hydrophobic coating 510, but this can be overcome by passivating any surfaces of the gold that will contact the hydrophobic coating 510. Such passivation can be achieve, for example, by reacting the gold surfaces with thiol-containing molecules. Similarly, if the wires of the mesh electrode 508 comprise aluminum, surfaces that will contact the hydrophobic coating 510 can be passivated. Aluminum passivation can be achieved, for example, by surface oxidation (e.g., by plasma treatment of the exposed surfaces of the aluminum wires in an oxygen plasma chamber).

The hydrophobic coating 510 can comprise an organofluorine polymer, which can optionally include at least one perfluorinated segment. For example, the organofluorine polymer can comprise polytetrafluoro-ethylene (PTFE) (i.e., Teflon®) or poly(2,3-difluoromethylenyl-perfluorotetrahydrofuran) (i.e., Cytop™). The chemical structure of poly(2,3-difluoromethylenyl-perfluorotetrahydrofuran) is as follows:

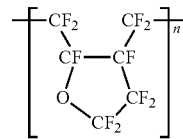

Hydrophobic coatings 510 that comprise an organofluorine polymer, such as polytetrafluoro-ethylene (PTFE) or poly(2,3-difluoromethylenyl-perfluorotetrahydrofuran), can have a thickness of at least about 10 nm, at least about 15 nm, at least about 20 nm, at least about 25 nm, at least about 30 nm, or at least about 35 nm. For example, the hydrophobic coating 510 can have a thickness of about 25 nm to about 40 nm.

The hydrophobic layer 510 can comprise a densely packed monolayer of amphiphilic molecules covalently bonded to molecules of the top surface of the dielectric layer 506 (and/or surfaces of the mesh electrode 508 that are not embedded in the dielectric layer 506). Such amphiphilic molecules can each comprise a siloxane group, a phosphonic acid group, or a thiol group, and the respective siloxane groups, phosphonic acid groups, and thiol groups can form the covalent bonds with the molecules of the dielectric layer 506. As used herein, a "densely packed monolayer" of amphiphilic molecules refers to a monolayer of amphiphilic molecules having sufficient two-dimensional packing density so as to create a hydrophobic barrier between a surface to which the monolayer is bound and a hydrophilic liquid. As persons skilled in the art will appreciate, the appropriate packing density of a densely packed monolayer will depend on the amphipathic molecules used. A densely packed monolayer comprising alkyl-terminated siloxane, for example, will typically comprise at least $1\times10^{14}$ molecules/$cm^2$ (e.g., at least $1.5\times10^{14}$, $2.0\times10^{14}$, $2.5\times10^{14}$, or more molecules/$cm^2$).

The amphiphilic molecules of a hydrophobic layer 510 can comprise long-chain hydrocarbons, which can be unbranched. Thus, the amphiphilic molecules can comprise alkyl-terminated siloxane, alkyl-termination phosphonic acid, or alkyl-terminated thiol. The long-chain hydrocarbons can comprise a chain of at least 10 carbons (e.g., at least 16, 18, 20, 22, or more carbons). In addition, the amphiphilic molecules can comprise fluorinated (or perfluorinated) carbon chains. Thus, for example, the amphiphilic molecules can comprise fluoroalkyl-terminated siloxane, fluoroalkyl-terminated phosphonic acid, or fluoroalkyl-terminated thiol. The fluorinated carbon chains can have the chemical formula $CF_3-(CF_2)_m-(CH_2)_n-$, wherein m is at least 2, n is 0, 1, 2, or greater, and m+n is at least 9. For example, the fluorinated carbon chains can have the chemical formula $CF_3$—$(CF_2)_7$—$(CH_2)_2$—.

The monolayer of amphiphilic molecules, and thus the hydrophobic layer 510 formed from such a monolayer, can have a thickness of less than about 5 nanometers (e.g., about 1.0 to about 4.0 nanometers, about 1.5 to about 3.0 nanometers, or about 2.0 to about 2.5 nanometers).

Hydrophobic layers 510 formed from a monolayer of amphiphilic molecules can be optionally patterned, such that select regions are relatively hydrophilic compared to the remainder of the hydrophobic layer 510. This can be achieved, for example, by applying a voltage potential across the SSOEW-configured substrate 500 for a period of time. Regions on the hydrophobic layer 510 that are illuminated and contacting an aqueous droplet when the voltage potential is applied to the SSOEW-configured substrate 500 will thereafter exhibit less hydrophobic (or relatively hydrophilic) characteristics relative to the regions on the hydrophobic layer 510 that were not contacting an aqueous droplet when the voltage potential was applied. Without intending to be bound by theory, it is believed that the relatively hydrophilic regions comprise water molecules that have intercalated into the amphiphilic monolayer. As persons skilled in the art will appreciate, the requisite voltage potential for patterning the hydrophobic layer 510 will vary depending upon the exact design of the SSOEW-configured substrate 500 (e.g., the thickness and impedances of the dielectric layer 506 and the photoconductive layer 504, and the like). In certain embodiments, the voltage potential required to pattern the hydrophobic layer 510 is at least about 50 ppV (e.g., at least about 60 ppV, at least about 65 ppV, at least about 70 ppV, at least about 75 ppV, or at least about 80 ppV).

The photoconductive (or photosensitive) layer 504 (shown in FIGS. 3A-B, 4A, and 5A-B) of an SSOEW-configured substrate 500 can comprise a semiconductor material that exhibits decreased electrical resistance in response to stimulation by electromagnetic radiation. The electromagnetic radiation can be, for example, radiation having a wavelength in the visible spectrum and/or the near-infrared or near-ultraviolet spectra. The semiconductor material can comprise silicon. For example, the photoconductive layer 504 can comprise hydrogenated amorphous silicon (a-Si:H). The a-Si:H can comprise, for example, about 8% to 40% hydrogen (i.e., calculated as 100*(the number of hydrogen atoms)/(total number of hydrogen and silicon atoms)). The a-Si:H photoconductive layer 504 can have a thickness of at least about 500 nm (e.g., at least about 600 nm to about 1400 nm, about 700 nm to about 1300 nm, about 800 nm to about 1200 nm, about 900 nm to about 1100 nm, or about 1000 nm).

When the SSOEW-configured substrate 500 has a photoconductive layer 504 formed from a layer of a-Si:H, the substrate 500 can optionally include floating electrode pads located between the photoconductive layer 504 and the dielectric layer 506. Such floating electrode pads have been described, for example, in U.S. Pat. No. 6,958,132 (Chiou et al.).

Alternatively, the photoconductive layer 504 can comprise a plurality of conductors, each conductor controllably connectable to the planar electrode 502 of the SSOEW-configured substrate 500 via a phototransistor switch. Conductors controlled by phototransistor switches are well-known in the art and have been described, e.g., in U.S. Patent Application No. 2014/0124370 (Short et al.), the contents of which are incorporated herein by reference.

As will be appreciated by persons skilled in the art, the thickness of the photoconductive layer 504 can be varied in accordance with other components of the SSOEW-configured substrate 500, such as the thickness of the dielectric layer 506, so as to achieve suitable differences between the impedance of the dielectric layer 506 and the impedance of the photoconductive layer 504 when the SSOEW-configured substrate 500 is in both the "on" or "illuminated" state (i.e., a voltage potential is applied across the substrate 500 and the photoconductive layer 504 is illuminated) and the "off" or "dark" state (i.e., a voltage potential is applied across the substrate 500 and the photoconductive layer 504 is not illuminated). For example, the impedance of the dielectric layer 506 can be tuned to have an impedance that is at least 10 times (e.g., at least 15 times, at least 20 time, at least 25 times, at least 30 times, or more) greater than the impedance of the photoconductive layer 504 in the illuminated state, and at least 10 times (e.g., (e.g., at least 15 times, at least 20 time, at least 25 times, at least 30 times, or more) smaller than the impedance of the photoconductive layer 504 in the dark state. As a particular example, the impedance of the dielectric layer 506 can be about 10 kOhms to about 50 kOhms, and the impedance of the photoconductive layer 504 (e.g., an a-Si:H photoconductive layer) can be tuned to at least about 0.5 MOhms in the dark/off state and about 1 kOhms or less in the illuminated/on state. These are only examples, but they illustrate how the impedances can be tuned to achieve a SSOEW-configured substrate 500 displaying robust on/off performance.

The SSOEW-configured substrate 500 can comprise a planar electrode 502. The planar electrode 502 can comprising a conductive layer 502a and, optionally, a support 502b. For example, the conductive layer 502a can comprise (or consist essentially of, or consist of) a layer of indium-tin-oxide (ITO). Alternatively, the conductive layer 502a can comprise a layer of electrically conductive silicon (e.g., highly p- or n-doped silicon). The support 502b can be, for example, a layer of glass or some other insulating material, such as a plastic. The planar electrode 502 can comprise a single electrode (e.g., a single conductive layer 502a) or a plurality of individually addressable electrodes (e.g., two or more conductive layers 502a that are spatially separated from one another). The individually addressable electrodes can be, for example, located on different regions of a common support 502b, thereby providing a SSOEW-configured substrate 500 having discrete SSOEW-configured regions. The individually addressable electrodes can be connectable to one or more AC voltage sources via corresponding transistor switches.

The planar electrode 502 (or a conductive layer 502a thereof) and the mesh electrode 508 of the SSOEW-configured substrate 500 can be configured to be connected to opposing terminals of an AC voltage source, as shown in FIGS. 3B, 4A, and 5B. When the planar electrode 502 (or a conductive layer 502a thereof) and the mesh electrode 508 of the SSOEW-configured substrate 500 are connected to opposing terminals of an AC voltage source (shown in FIGS. 3B, 4A, and 5B), the substrate 500 is capable of applying an electrowetting (EW) force to aqueous droplets in contact with the hydrophobic coating 510 of the substrate 500. Application of the force is controlled by illuminating specific locations in the photoconductive layer 504 of the substrate 500. The AC voltage used to achieve such EW-based movement of droplets will vary depending upon the exact construction of the substrate 500, and may reflect the thickness and impedance of the dielectric layer 506 and the photoconductive layer 504. In certain embodiments, a AC voltage potential of at least 10 Volts peak-to-peak (ppV) (e.g., about 10 ppV to about 80 ppV, about 20 ppV to about 70 ppV, about 25 ppV to about 60 ppV, about 30 ppV to about 50 ppV, or about 40 ppV) is applied to the substrate in order to achieve droplet movement. The frequency of the AC voltage potential also impacts the ability of the substrate 500 to achieve EW-based movement of droplets. Again, the frequency requirements can vary depending upon the specific construction of the substrate 500. In certain embodiments, the AC voltage potential required to achieve droplet movement has a frequency of about 1 kHz to about 100 kHz (e.g., about 2 kHz to about 80 kHz, about 3 kHz to about 60 kHz, about 4 kHz to about 40 kHz, about 5 kHz to about 35 kHz, about 6 kHz to about 30 kHz, about 7 kHz to about 25 kHz, about 8 kHz to about 20 kHz, about 9 kHz to about 15 kHz, or about 10 kHz). In certain embodiments, the voltage potential applied to the substrate 500 to achieve droplet movement is about 30 ppV to about 60 ppV (e.g., about 35 ppV to about 50 ppV, or about 40 ppV) and has a frequency of about 5 kHz to about 35 kHz (e.g., about 5 kHz to about 20 kHz, or about 10 kHz). By applying the foregoing AC voltage potentials to the SSOEW-configured substrates of the invention, droplets can be moved about the surface of the hydrophobic coating 510 at a rate of at least 0.01 mm/sec (e.g., at least 0.05 mm/sec, at least 0.1 mm/sec, at least 0.5 mm/sec, at least 0.6 mm/sec, at least 0.7 mm/sec, at least 0.8 mm/sec, at least 0.9 mm/sec, at least 1.0 mm/sec, at least 1.5 mm/sec, at least 2.0 mm/sec, at least 2.5 mm/sec, at least 3.0 mm/sec, at least 3.5 mm/sec, at least 4.0 mm/sec, at least 4.5 mm/sec, at least 5.0 mm/sec, or more).

Figure 4B:
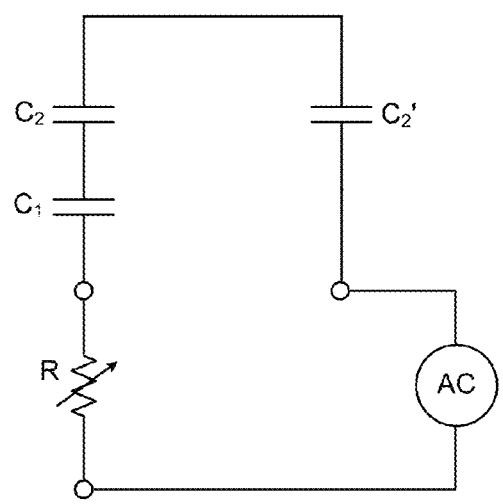
FIG. 4B provides an isolated view of the electrical circuit diagram of FIG. 4A.

FIGS. 4A-B illustrate circuit models for a SSOEW-configured substrate 500 of the invention. As shown, a conductive layer 502a of the planar electrode 502 is electrically connected to droplet 520, which is resting on the hydrophobic coating 510, via the photoconductive layer 504, the dielectric layer 506, and the hydrophobic coating 510. The resistance in the photoconductive layer 504 is variable, depending on whether or not light is incident on a particular region of the photoconductive layer 504, and thus there is a voltage drop across the photoconductive layer 504 which varies depending upon the resistance R of the photoconductive layer 504. The dielectric layer 506 and the hydrophobic coating 510 function as capacitors C1 and C2, respectively, in the electrical circuit. In addition, there is capacitive connection C2' between the droplet 520 and the mesh electrode 510. The AC voltage source completes the electrical circuit by connecting to both the mesh electrode 508 and the conductive layer 502a of the planar electrode 502. Voltage dropped across the dielectric layer 506 results in droplet actuation. Voltage dropped across shunt connections (e.g., between the conductive layer 502a of the planar electrode 502 and the wires of the mesh electrode 508, through the dielectric layer 506 and the photoconductive layer 504) (not shown) are not useful for actuation. Accordingly, it is advantageous to minimize the area of the dielectric layer 506 that is shielded from the droplet 520 by the wires of the mesh electrode 508. Assuming a linear fill factor $\beta$ for the mesh electrode 508, the electrowetting force is approximately $(1-\beta)$ times the electrowetting force of an OEW device having a top electrode. Thus, for example, for a mesh electrode 508 made from 10 micron-wide wires on a 1 mm pitch yields a linear fill factor $\beta=99\%$. Accordingly, by keeping the wires of the mesh electrode 508 thin and spread out, the electrowetting force of the SSOEW-configured substrate 500 is substantially unchanged relative to an OEW device having a planar top electrode.

Figure 9:
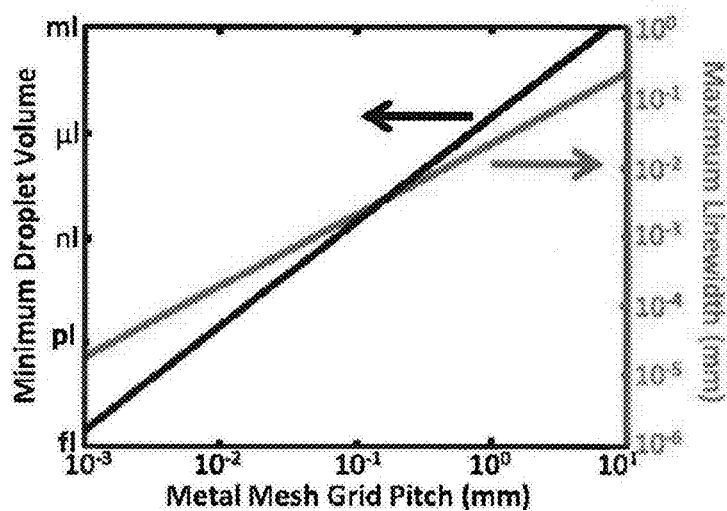
FIG. 9 is a graph showing estimates of the minimum volume of a droplet that can be moved with a SSOEW-configured substrate having a mesh ground electrode with a given pitch. The graph also shows the maximum wire width that provides >90% EW force versus a given pitch.

The pitch of the wires in the mesh electrode 508 also impacts the size of the droplets that can be moved on the SSOEW-configured substrate 500. In general, the pitch of the wires should be smaller than the diameter of the droplet, otherwise the droplet can get trapped between wires. FIG. 9 shows the relationship between the minimum droplet volume and the pitch of the mesh electrode 508. As can be seen, the movement of nanoliter-scale droplets (e.g., 100 nL up to 500 nL/droplet) will typically require the wires of the mesh electrode 508 to have a pitch of about 100 microns to about 500 microns. Likewise, the movement of picoliter-scale droplets (e.g., 100 pL to 500 pL/droplet) will typically require the wires of the mesh electrode 508 to have a pitch of about 5 microns to about 50 microns. The relationship between the pitch of the wires and the maximum wire width that allows for a linear fill factor $\beta$ of at least 90% is also shown in FIG. 9.

Microfluidic Devices Having a SSOEW-Configured Substrate Base.

The SSOEW-configured substrates of the invention can be integrated into microfluidic devices. For example, the SSOEW-configured substrate can provide a base for the microfluidic device. The microfluidic device can further include walls, disposed upon the substrate/base, that extend vertically upward from the substrate/base. Together, the walls and the substrate/base can define a microfluidic circuit configured to hold a liquid medium. The liquid medium can be, for example, a hydrophobic liquid, such as an oil. In addition, the microfluidic circuit can hold a droplet of liquid, such as an aqueous medium. Typically, the liquid medium and the liquid of the droplet are selected to be immiscible liquids.

Figure 7:
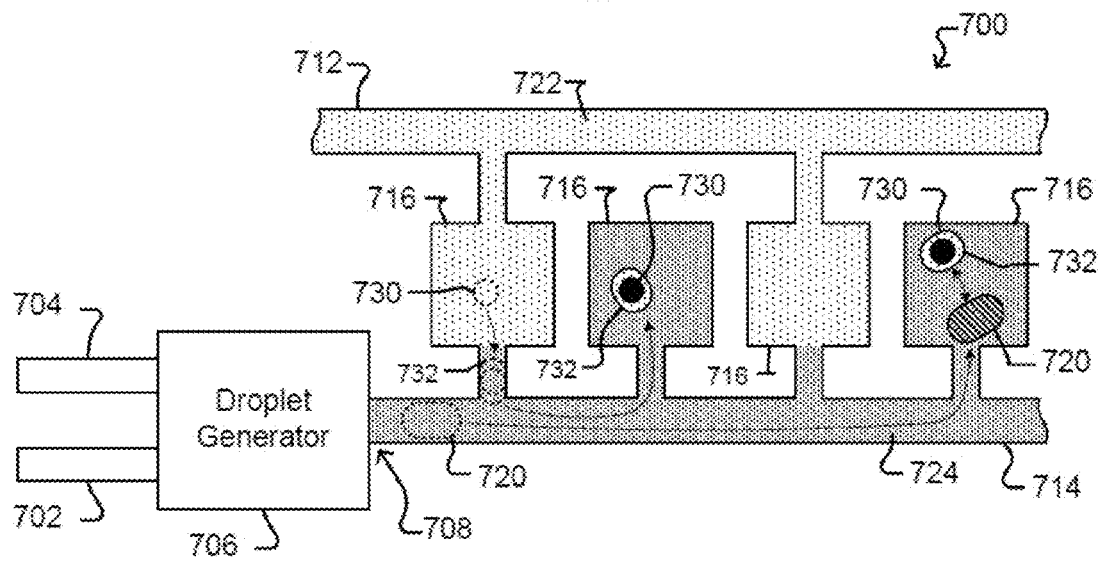
FIG. 7 is a top-down view of a microfluidic apparatus having multiple microfluidic channels, chambers that open off of the microfluidic channels, and a droplet generator, according to certain embodiments of the invention. In this embodiment, one microfluidic channel contains an aqueous medium (lighter color), while the microfluidic channel connected to the droplet generator contains a hydrophobic medium (darker color). The chambers likewise contain either an aqueous medium or a hydrophobic medium.
Figure 8:
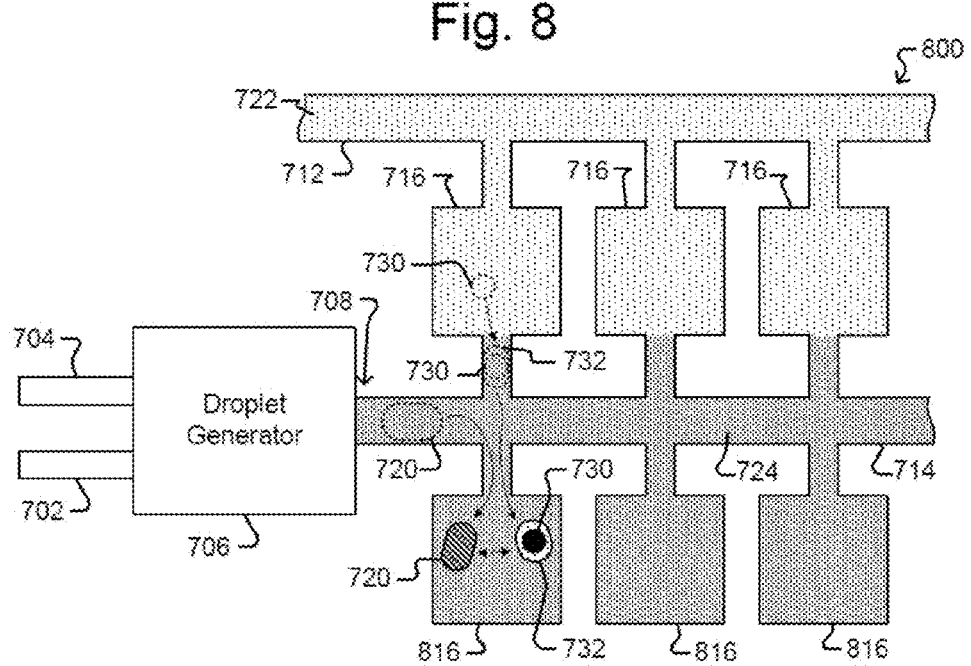
FIG. 8 is a top-down view of a microfluidic apparatus having multiple microfluidic channels, chambers that open off of the microfluidic channels, and a droplet generator, according to other embodiments of the invention.

The walls of the microfluidic device can define one or more flow regions, which can be microfluidic channels. In addition, the walls can further define one or more (e.g., a plurality of) chambers in the microfluidic device, each fluidically connected to and opening off of at least one flow region (or microfluidic channel). One or more such chambers can be a sequestration pen. Thus, for example, the walls can define a single microfluidic channel and a plurality of chambers fluidically connected thereto, or a plurality of microfluidic channels with each channel fluidically connected to a plurality of chambers. Furthermore, each chamber can be fluidically connected to more than one microfluidic channel, as illustrated in FIGS. 7 and 8.

The walls of the microfluidic device can comprise a structural polymer. As used herein, the term "structural polymer" refers to materials that comprise a polymer and have sufficient structural rigidity so as to form structures that have a height that is greater than a width of the structure. For example, a structural polymer can form a wall which, when viewed in cross-section, has an aspect ratio of about 1:1.1, about 1:1.2, about 1:1.3, about 1:1.4, about 1:1.5, about 1:2, about 1:2.5, about 1:3, about 1:3.5, about 1:4, about 1:4.5, about 1:5, or greater. The structural polymer can comprise (or consist essentially of, or consist of), for example, a silicon-based polymer, such as polydimethylsiloxane (PDMS) or photo-patternable silicone (PPS), both available from Dow Corning. Alternatively, the walls can comprise an epoxy-based adhesive. The epoxy-based adhesive can be, for example, SU-8 or equivalent types of adhesives.

The walls of the microfluidic device can have a height of at least about 30 microns, at least about 40 microns, at least about 50 microns, at least about 60 microns, at least about 70 microns, at least about 80 microns, at least about 90 microns, at least about 100 microns, or more. Thus, for example, the height of the walls can be about 30 to about 60 microns, about 40 to about 80 microns, about 50 to about 100 microns, about 60 to about 120 microns, about 70 to about 140 microns, about 75 to about 150 microns, about 80 to about 160 microns, about 90 to about 180 microns, or about 100 to about 200 microns. In addition, the walls can have a cross-sectional width of about 10 to about 50 microns, or about 20 to about 40 microns.

The microfluidic device can optionally include a cover, which can be disposed on the walls. The cover can be substantially parallel to the substrate/base. Together, the substrate, the walls, and the cover can define an enclosure configured to contain a liquid medium. The liquid medium can be, for example, a hydrophobic liquid, such as an oil. In addition, the enclosure can contain a droplet of liquid, such as an aqueous medium. Typically, the liquid medium and the liquid of the droplet are selected to be immiscible liquids.

The cover of the microfluidic device can be made, all or in part, from the same material(s) as the walls. Thus, the cover can comprise a structural polymer, such as a silicon-based polymer (e.g., PDMS or PPS). Alternatively, the cover can be made, all or in part, from material(s) that differ from the wall material(s), such as rigid material (e.g., glass). The cover can be made, at least in part, from material that is piercable, so that droplets can be introduced or removed from enclosure by a piercing structure, such as a needle. The cover can comprise a hydrophobic coating, such as the hydrophobic coating 510 of the SSOEW-configured substrate 500.

In some embodiments, the cover can be a SSOEW-configured substrate 500. Thus, the microfluidic device can have both the base and the cover configured to provide an electrowetting force to an aqueous droplet located within the enclosure.

A microfluidic device of the invention can be manufactured, for example, by: bonding wall material to the dielectric layer 506 (and, if exposed, the mesh electrode 508) of a SSOEW-configured substrate 500 that is lacking the hydrophobic coating 510; optionally bonding the wall material to a cover; and applying the hydrophobic coating 510 on the portions of the dielectric layer 506 (and mesh electrode 508) that remain exposed after bonding of the wall material. For the following discussion regarding the application of the hydrophobic coating 510 to the dielectric layer 506 (and, if exposed, the mesh electrode 508), it should be understood that the referenced SSOEW-configured substrate 500 (or simply substrate 500) may not include the hydrophobic coating 510, but such should be evident from the nature of the discussion.

The wall material can be applied directly to the dielectric layer 506 (and, if exposed, the mesh electrode 508), or it can be applied to the cover (if present) and then subsequently applied to the dielectric layer 506 (and mesh electrode 508). The wall material can be applied initially as a continuous layer and then patterned (e.g., by photo-patterning or etching, depending upon the type of wall material used).

The hydrophobic coating 510 can be applied via dip/spin coating, spray coating, vapor deposition, or the like. For example, a hydrophobic coating 510 comprising polytetrafluoro-ethylene (PTFE) (i.e., Teflon®) or poly(2,3-difluoromethylenyl-perfluorotetrahydrofuran) (i.e., Cytop™) can be applied by spin coating. Deposition of amphiphilic molecules, such as alkyl- or fluoroalkyl-terminated siloxanes or alkyl- or fluoroalkyl-terminated thiols can be achieved by vapor deposition.

Application of the hydrophobic coating 510 by dip/spin coating generally comprises dipping the dielectric layer 506 of the SSOEW-configured substrate 500 into a solution comprising molecules of the hydrophobic coating diluted in a solvent (e.g., polytetrafluoro-ethylene (PTFE) or poly(2,3-difluoromethylenyl-perfluorotetrahydrofuran)), spinning the coated substrate 500 in a centrifuge, and then baking the substrate at a temperature high enough and for a duration long enough to boil off the solvent. The exact conditions will vary with the coating being applied. With Teflon® AF (Dupont), the coating is provided at a concentration of about 6% and is diluted in a fluorinated oil, such as Fluorinert-40 (FC-40) or Fluorinert-77 (FC-77), to a final concentration of less than 0.5% (e.g., about 0.2%). With Cytop™ (CTL-09M, Dupont), the coating is provided at a concentration of about 9% and is diluted in CTSOLV-180 or CTSOLV-100E BP Perfluorinated Solvent to a final concentration of about 2% or less (e.g., about 0.1% to about 2.0%). Of course, these Cytop™-specific solvents could be replaced by conventional fluorinated oils, such as FC-40 or FC-77. After the dielectric layer 506 of the substrate 500 is dipped in the diluted coating solution, the substrate can be centrifuged at a speed (e.g., about 3000 RPM) and for a duration of time (e.g., at least 15 seconds, about 20 seconds to about 1 minute, or about 30 seconds) sufficient to produce a substantially uniform coating on the dielectric layer 506. Excess solvent is then baked off at a temperature appropriate for the solvent used and for a duration sufficient to achieve the desired coating (e.g., at least 20 minutes, about 20 minutes to about 1 hour, or about 30 minutes). The baking temperature for CTSOLV-180 and CTSOLV-100E, for example, are about 180° C. and 100° C., respectively.

Application of a monolayer of amphiphilic molecules can be performed by vapor deposition, with the exact procedure varying according to the amphiphilic molecules being used. For example, for alkyl- or fluoroalkyl-terminated siloxanes, the deposition can be performed at a temperature of at least about 110° C. (e.g., at least about 120° C., at least about 130° C., at least about 140° C., at least about 150° C., at least about 160° C., etc.), for a period of at least about 15 hours (e.g., at least about 20 hours, at least about 25 hours, at least about 30 hours, at least about 35 hours, at least about 40 hours, or at least about 45 hours). Such vapor deposition is typically performed under vacuum and in the presence of a water source, such as a hydrated salt (e.g., $MgSO_4 \cdot 7H_2O$). Typically, increasing the temperature and duration of the vapor deposition produces improved characteristics of the hydrophobic layers 122 and 142, but such parameters can be significantly impacted by the vacuum chamber used. The vapor deposition process can be optionally improved by pre-cleaning the dielectric layer. Such pre-cleaning can include a solvent bath, such as an acetone bath, an ethanol bath, or both (e.g., sequentially). The pre-cleaning can include sonication during the solvent bath. Alternatively, or in addition, such pre-cleaning can include treating the substrate 500 in an oxygen plasma cleaner. The oxygen plasma cleaner can be operated under vacuum conditions, at a power setting (e.g., 100 W) and for a duration (e.g., at least 30 seconds, at least 45 seconds, at least 60 seconds, or more) sufficient to produce a clean surface on the dielectric layer 506.

Application of a monolayer of amphiphilic molecules can be performed by dip coating as well. For example, alkyl- or fluoroalkyl-terminated phosphonic acids or alkyl- or fluoroalkyl-terminated thiols can be applied by dip coating. The dip coating process can be optionally improved by pre-cleaning the dielectric layer 506 of the SSOEW-configured substrate 500. Such pre-cleaning can include a solvent bath, such as an acetone bath, an ethanol bath, or both (e.g., sequentially). The pre-cleaning can include sonication during the solvent bath. Alternatively, or in addition, such pre-cleaning can include treating the substrate 500 in an oxygen plasma cleaner. The oxygen plasma cleaner can be operated under vacuum conditions, at a power setting (e.g., 100 W) and for a duration (e.g., at least 30 second, at least 45 seconds, at least 60 seconds, or more) sufficient to produce a clean surface on the dielectric layer 506. The substrate 500 is then submerged in a freshly prepared 10 mM solution of the amphiphilic molecule in ethanol for a period of time sufficient to achieve formation of the desired densely-packed monolayer. After removing the substrate 500 from the solution, the surfaces of the substrate 500 are rinsed with an excess amount of ethanol.

Methods for Moving Droplets in a Microfluidic Device.

FIG. 7 illustrates an example of a microfluidic device 700 which comprises: a microfluidic circuit having microfluidic channels 712, 714 and a plurality of chambers 716; and a droplet generator 706 for providing fluidic droplets 720 to the microfluidic circuit. Microfluidic channel 714 is configured to hold a first fluidic medium 724. Typically, the first fluidic medium is a hydrophobic fluid, such as an oil (e.g., a silicone oil or a fluorinated oil). Microfluidic channel 714 is connected to the droplet generator 706 via an interface 708, which allows channel 714 to receive droplets 720 generated by the droplet generator 706. The received droplets 720 comprise a liquid which is immiscible in the first fluidic medium 724. Typically, the received droplets will comprise an aqueous medium, which may contain micro-objects, such as cells or beads, or reagents that are soluble in aqueous media. Microfluidic channel 714 is also connected to each of the plurality of chambers 716, facilitating movement of received droplets 720 (as well as droplets 732 pulled from a reservoir of fluid immiscible in the first fluidic medium 724) into and between chambers 716.

Microfluidic channel 712 of device 700 is connected to a subset of chambers 716, and thus is indirectly connected to microfluidic channel 714 via such chambers 716. As illustrated, microfluidic channel 712 and the chambers 716 connected thereto contains a fluidic medium 722 which is immiscible in the first fluidic medium 724. Thus, for example, fluidic medium 722 can be an aqueous medium, such as a cell culture medium. When fluidic medium 722 is a cell culture medium, the chambers 716 that contain culture medium can be used as culture chambers for growing cells, and microfluidic channel 712 can be a perfusion channel that provides a flow of fresh culture medium. As discussed herein, the flow of fresh culture medium in a perfusion channel can, via diffusion of molecules between the perfusion channel and a culture chamber, provide nutrients to the chamber and remove waste from the chamber, thus facilitating continued cell growth.

FIG. 8 illustrates another example of a microfluidic device 800 of the invention. Device 800 comprises: a microfluidic circuit having microfluidic channels 712, 714, a first plurality of chambers 816, and a second plurality of chambers 716; and a droplet generator 706 for providing fluidic droplets 720 to the enclosure. FIG. 8 presents a variation on the microfluidic apparatus 700 shown in FIG. 7, wherein chambers 716 contain a medium 722 that is immiscible in the first fluidic medium 724 (located in microfluidic channel 714) and are located directly across the microfluidic channel 714 from corresponding chambers 814. This configuration facilitates movement of fluid droplets 732 (optionally containing micro-objects 730 or biological material) from a select chamber 716 to the corresponding chamber 816, where the fluid droplets (and any micro-objects 730 or biological material) can be processed.

The microfluidic circuits formed by the microfluidic channels 712, 714 and chambers 716, 816 are merely examples, and many other configurations of channels and chambers are encompassed by the invention. For example, in each of apparatuses 700 and 800, microfluidic channel 712 and the chambers 716 directly connected to channel 712 are optional features. Thus, apparatuses 700 and 800 can lack perfusion channels and culture chambers.

In embodiments where microfluidic channel 712 is present, the substrate which helps to define channel 712 and/or directly connected chambers 716 (e.g., by forming the base of the channel and/or chambers) can have an electrowetting configuration. Alternatively, however, the substrate which helps to define the channel 712 and/or directly connected chambers 716 can lack an electrowetting configuration (e.g., and instead can have a DEP configuration, or neither an electrowetting nor a DEP configuration). In embodiments in which microfluidic channel 712 is present, and the substrate which helps to define channel 712 and/or directly connected chambers 716 has an electrowetting configuration, the hydrophobic coating 510 of the substrate can be patterned to be more hydrophilic than the hydrophobic coating of the substrate which helps to define channel 714. The increased hydrophilicity can be achieved, for example, as discussed above.

The droplet generator 706 and any microfluidic circuit to which it provides droplets can be part of a microfluidic device (either an integral part or connected thereto), which can be like any of the microfluidic devices illustrated in the drawings or described herein. Although one droplet generator 706 is shown in FIGS. 7 and 8, more than one such droplet generator 706 can provide droplets to the microfluidic circuit of apparatuses 700 and 800. The droplet generator 706 itself can include an electrowetting configuration, and can thus comprise a substrate having a photoresponsive layer, which can comprise a-Si:H (e.g., as illustrated in U.S. Pat. No. 6,958,132), a photo-actuated circuit substrate (e.g., as illustrated in U.S. Patent Application Publication No. 2014/0124370), a phototransistor-based substrate (e.g., as illustrated in U.S. Pat. No. 7,956,339), or an electrically-actuated circuit substrate (e.g., as illustrated in U.S. Pat. No. 8,685,344). Alternatively, the droplet generator can have a T- or Y-shaped hydrodynamic structure (e.g., as illustrated in U.S. Pat. Nos. 7,708,949, 7,041,481 (reissued as RE41,780), 2008/0014589, 2008/0003142, 2010/0137163, and 2010/0172803). All of the foregoing U.S. patent documents are incorporated by reference herein in their entirety.

As shown, the droplet generator 706 can comprise one or more fluidic inputs 702 and 704 (two are shown but there can be fewer or more) and a fluidic output 708, which can be connected to the microfluidic channel 714. Liquid media 722, 724, biological micro-objects 730, reagents, and/or other biological media can be loaded through the inputs 702 and 704 into the droplet generator 706. The droplet generator 706 can generate and output into the channel 714 droplets 720 of the liquid medium 722 (which can, but need not, contain one or more biological micro-objects 730), reagents, or other biological medium. If the channel 714 has an electrowetting configuration, the droplets 720 can be moved in the channel 714 utilizing electrowetting (or optoelectrowetting). Alternatively, the droplets 720 can be moved in the channel 714 by other means. For example, the droplets 720 can be moved in the channel 714 using fluidic flow, gravity (if the microfluidic device includes a cover), or the like.

As discussed above, the microfluidic channel 714 and select chambers 716/816 can be filled with a first fluidic medium 724, and microfluidic channel 712 and chambers 716 connected directly thereto can be filled with a second fluidic medium 722. The second fluidic medium 722 (hereinafter an "aqueous medium") can be an aqueous medium, such as a sample medium for maintaining, culturing, or the like biological micro-objects 730. The first fluidic medium 724 (hereinafter an "immiscible medium") can be a medium in which the aqueous medium 722 is immiscible. Examples of the aqueous medium 722 and the immiscible medium 724 include any of the examples discussed above for various media.

The droplet generator 706 can be utilized to load biological micro-objects and/or facilitate the running of biochemical and/or molecular biological workflows on the microfluidic apparatus. FIGS. 7 and 8 illustrate non-limiting examples. By using a droplet generator, the apparatus can have an electrowetting configuration throughout the fluidic circuit.

FIGS. 7 and 8 illustrate an example in which the droplet generator 706 generates a droplet 720 comprising a reagent (or other biological material). The reagent-containing droplet 720 can be moved through the microfluidic channel 714 and into one of the chambers 716/816 containing the immiscible medium 724. Prior to or after moving the reagent-containing droplet 720 into one of the chambers 716/816, one or more micro-objects 730 in one or more droplets 732 can be moved into the same chambers 716/816. The reagent-containing droplet 720 can then be merged with the droplet 732 containing the micro-object 730, allowing the reagents of droplet 720 to mix and chemically react with the contents of droplet 732. The one or more micro-object-containing droplets 732 can be supplied by the droplet generator 706 or can be obtained from a holding pen 716, as shown in FIGS. 7 and 8. The micro-object 730 can be a biological micro-object, such as a cell, which has optionally been cultured (e.g., in a chamber 716) prior to being moved to the processing chamber 716/816. Alternatively, the micro-object 730 can be a bead, such as an affinity bead that is capable of binding to molecules of interest in a sample (e.g., cell secretions present in culture medium 722 after the culture medium 722 has been used to culture one or more biological cells). In still other alternatives, the one or more droplets 732 can contain no micro-objects but only aqueous medium, such as culture medium 722, e.g., that contains cell secretions after the culture medium 722 has been used to culture one or more biological cells.

Various processes can be performed in a microfluidic device comprising a microfluidic circuit like any of devices 700 and 800.

At a step 402 of a process 400, a biological micro-object can be cultured in a holding pen filled with a sample medium (e.g., cell culture medium). For example, a micro-object 730 of FIG. 7 or 8 can be a biological cell and can be cultured in its chamber 716. Culturing can be generally as discussed above. For example, culturing can include perfusing the channel 712 with a culture medium 722. Step 402 can be performed over a specified period of time.

At a step 404, the cultured biological micro-object can be moved from the sample-medium-filled chamber 716 in which it was cultured to a chamber 716/816 filled with a medium in which the sample medium is immiscible. For example, the cultured micro-object 730 can be moved in a droplet 720 or 732 of culture medium 722 from one of the holding pens 716 into one of the holding pens 716/816, as illustrated in FIGS. 7 and 8, as discussed above.

At a step 406, the cultured biological micro-object can be subjected to one or more treatments or processes in the immiscible-medium-filled holding pen. For example, one or more droplets 720 containing one or more reagents can be produced by the droplet generator 706 and moved into an immiscible-medium-filled chamber 712/816 and merged with the droplet 732 containing the cultured biological micro-object 730, as shown in FIGS. 7 and 8 and discussed above. For example, a first reagent-containing droplet 720 can contain a lysing reagent. Merger of the droplet 732 containing the cultured biological micro-object 730 with the first reagent-containing droplet 720 containing lysing reagent, would result in the lysis of the cultured biological micro-object 730. In other words, a combined droplet (not shown) would be formed that contains a cell lysate from the cultured biological micro-object 730. Additional (e.g., second, third, fourth, etc.) reagent-containing droplets 720 could then be merged with the cell lysate-containing new droplet, so as to further process the cell lysate as desired.

In addition or as another example, one or more droplets containing one or more labeled capture micro-objects (not shown) having an affinity for a secretion or other material or materials of interest (e.g., nucleic acids such as DNA or RNA, proteins, metabolites, or other biological molecules) produced the cultured biological micro-object 730 can be generated by the droplet generator 706 and moved into the immiscible-medium-filled pen 716 or 816 and merged with the droplet of culture medium 722 containing the cultured biological micro-object 730 in a similar manner. In cases where the cultured biological micro-object 730 has already been lysed, capture micro-object-containing droplet 720 could contain one or more affinity beads (e.g., having affinity for nucleic acids, such as DNA, RNA, microRNAs, or the like) which, upon merger with the cell lysate-containing droplet in holding pen 716 or 816, could bind to target molecules present in the lysate.

At a step 408, the treated biological micro-object can be optionally processed. For example, if at step 406, a capture object (not shown) is moved into the immiscible-medium-filled chamber 716/816 with the cultured biological micro-object 730, the chamber 716/816 can be monitored at step 408 for a reaction (e.g., a fluorescent signal) indicative of a quantity of the material of interest bound to the labeled capture micro-object. Alternatively, such a capture micro-object (not shown) can be removed (e.g., in a droplet 722) from the chamber 716/816 and exported from the microfluidic device (not shown in FIG. 7 or 8) for subsequent analysis. As yet another example, the treated biological micro-object 730 can be removed (e.g., in a droplet 732) from the chamber 716/816 and exported from the microfluidic device (not shown) for subsequent analysis.

Although specific embodiments and applications of the invention have been described in this specification, these embodiments and applications are exemplary only, and many variations are possible. For example, the methods of FIG. 4 can be performed with respect to culture medium that contains cell secretions (e.g., after the culture medium 722 has been used to culture one or more biological cells). In such an embodiment, step 402 would remain the same, but step 404 would involve moving droplets 732 which can contain no micro-objects but only aqueous medium, such as culture medium 722 containing cell secretions, into immiscible-medium-containing chambers 716/816, and steps 406 and 408 would be performed with respect to such aqueous medium-containing droplets 732.

EXAMPLES

Example 1: Movement of Water Droplets on a SSOEW-Configured Substrate

The movement of a 1 microliter droplet of water (conductivity 10 mS/m) was successfully demonstrated on the device of FIG. 1. The device featured a gold mesh ground that had a thickness of substantially 50 nm. Individual wires of the mesh had a width of substantially 10 microns and pitch of substantially 2 mm (β=0.5%). Prior to operation, the surface of the device was primed with silicone oil to reduce friction.

An AC voltage bias was applied between the ITO electrode and the mesh ground electrode. Structured light was then projected onto the substrate proximal to the droplet being moved, such that the light at least partially contacted the droplet. Droplets were successfully moved by shifting the location of the structured light. In this experiment, light having a square shape roughly the same size as the droplet was used. A maximum velocity of 0.33 cm/s was measured using a 40 ppV bias at 10 kHz.

Figure 10:
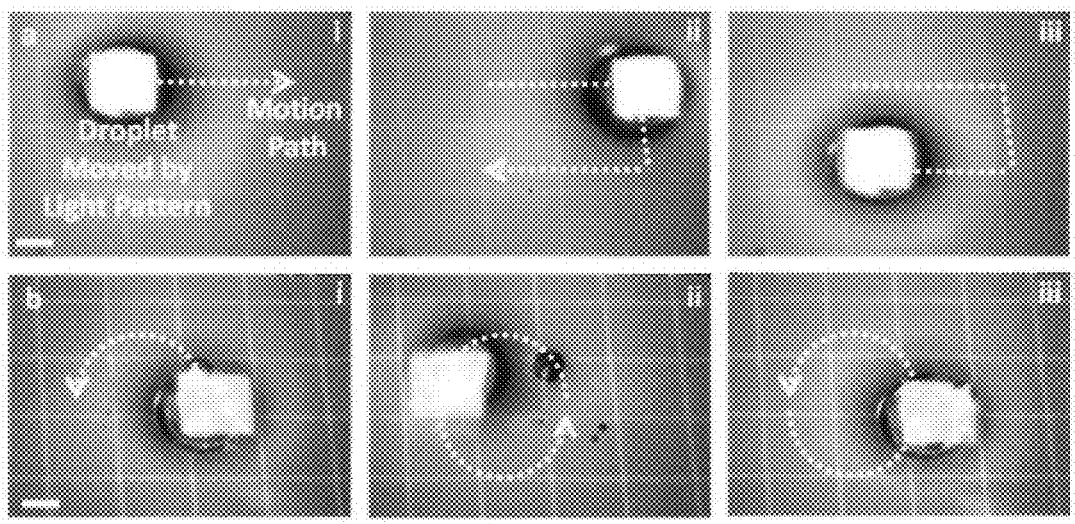
FIG. 10 shows images of droplet movement on a SSOEW-configured substrate according to certain embodiments of the invention. The images depict both rectangular movements (a(i)-(iii)) and circular movements (b(i)-(iii)).

The experiment confirmed that the droplets were free to move in any arbitrary direction so long as the droplet maintained electrical contact with the mesh ground electrode. As shown in FIGS. 10A-B, droplets were moved along rectangular and circular paths. In addition, it was possible to merge droplets using the device.

Example 2: Movement of PBS Droplets on a SSOEW-Configured Substrate

Subsequently, a SSOEW-configured substrate was built having a photoconductive layer of substantially 1 micron thickness, a first dielectric layer of substantially 150 nm thickness, a second dielectric layer of substantially 2.5 nm in thickness, a mesh electrode having wires consisting of a gold layer of substantially 25 nm in thickness with an underlying titanium layer of substantially 10 nm in thickness, and a hydrophobic coating comprising a monolayer of octadecyltrimethoxysilane. The photoconductive layer consisted essentially of hydrogenated amorphous silicon (a-Si:H), and the first and second dielectric layers were made from Alumina (i.e., aluminum oxide deposited by ALD). The mesh electrode was interposed between the first and second dielectric layers, and the wires of the mesh electrode were substantially 10 microns in width, with a pitch of approximately 300 microns.

A droplet of PBS (approximately 1.5 microliters in volume) was successfully moved around the surface of the SSOEW-configured substrate at a rate of about 1 mm/s. To achieve this movement, an AC voltage potential of about 40 ppV, with frequency of about 10 kHz, was applied to the substrate. The PBS droplet was moved through 3 cSt silicone oil (with the substrate submerged therein).

From the description herein, it will be appreciated that that the present disclosure encompasses multiple embodiments which include, but are not limited to, the following:

1. A substrate comprising: a planar electrode; a photoconductive layer; a dielectric layer; a mesh ground electrode; and a hydrophobic coating; wherein the photoconductive layer is interposed between the planar electrode and the dielectric layer, with a bottom surface of the photoconductive layer adjoining a top surface of the planar electrode and a top surface of the photoconductive layer adjoining a bottom surface of the dielectric layer; wherein the mesh ground electrode adjoins a top surface of the dielectric layer; wherein the planar electrode and the mesh ground electrode are configured to be connected to an AC voltage source; and wherein, when the planar electrode and the mesh ground electrode are connected to opposing terminals of the AC voltage source, the substrate is capable of applying an opto-electrowetting (OEW) force to aqueous droplets in contact with the hydrophobic coating.

2. The substrate of any preceding embodiment, wherein the substrate forms all or part of the base of a microfluidic device.

3. The substrate of any preceding embodiment, wherein the planar electrode comprises a metal conductor.

4. The substrate of any preceding embodiment, wherein the planar electrode comprises an indium-tin-oxide (ITO) layer.

5. The substrate of any preceding embodiment, wherein the planar electrode comprises a non-metal conductor.

6. The substrate of any preceding embodiment, wherein the planar electrode comprises a layer of conductive silicon.

7. The substrate of any preceding embodiment, wherein the photoconductive layer comprises hydrogenated amorphous silicon (a-Si:H).

8. The substrate of any preceding embodiment, wherein the photoconductive layer has a thickness of at least 500 nm.

9. The substrate of any preceding embodiment, wherein the photoconductive layer has a thickness of about 900 to 1100 nanometers.

10. The substrate of any preceding embodiment, wherein the dielectric layer comprises a metal oxide.

11. The substrate of any preceding embodiment, wherein the dielectric layer comprises aluminum oxide.

12. The substrate of any preceding embodiment, wherein the dielectric layer has a thickness of at least 125 nm.

13. The substrate of any preceding embodiment, wherein the dielectric layer was formed by atomic layer deposition.

14. The substrate of any preceding embodiment, wherein the dielectric layer is a composite dielectric layer having at least a first dielectric layer and a second dielectric layer, with a bottom surface of the first dielectric layer adjoining the photoconductive layer.

15. The substrate of any preceding embodiment, wherein the mesh ground electrode is interposed between the first dielectric layer and the second dielectric layer.

16. The substrate of any preceding embodiment, wherein the composite dielectric layer has a thickness of at least 125 nm.

17. The substrate of any preceding embodiment, wherein the first and second dielectric layers both comprise a metal oxide.

18. The substrate of any preceding embodiment, wherein the first and second dielectric layers both comprise aluminum oxide.

19. The substrate of any preceding embodiment, wherein the first and second dielectric layers are both formed by atomic layer deposition.

20. The substrate of any preceding embodiment, wherein the first dielectric layer has a thickness of about 125 nm to about 175 nm 21. The substrate of any preceding embodiment, wherein the second dielectric layer has a thickness of less than 10 nm.

22. The substrate of any preceding embodiment, wherein the first dielectric layer has a top surface adjoining a bottom surface of the mesh ground electrode.

23. The substrate of any preceding embodiment, wherein the first dielectric material forms a lattice.

24. The substrate of any preceding embodiment, wherein the top surface of the first dielectric layer is substantially contiguous with the bottom surface of the mesh ground electrode.

25. The substrate of any preceding embodiment, wherein the first dielectric layer is made from a material having a dielectric constant $\in1$, the second dielectric layer is made from a material having a dielectric constant $\in2$, and $\in1$ is less than $\in2$.

26. The substrate of any preceding embodiment, wherein the first dielectric layer comprises a metal oxide.

27. The substrate of any preceding embodiment, wherein the first dielectric layer comprises aluminum oxide.

28. The substrate of any preceding embodiment, wherein the first dielectric layer has a thickness of about 50 nm to about 150 nm.

29. The substrate of any preceding embodiment, wherein the second dielectric layer comprises a non-metal oxide.

30. The substrate of any preceding embodiment, wherein the second dielectric layer comprises silicon oxide.

31. The substrate of any preceding embodiment, wherein the composite dielectric layer comprises a first dielectric layer, a second dielectric layer, and a third dielectric layer, with the second dielectric layer interposed between the first and third dielectric layers.

32. The substrate of any preceding embodiment, wherein the first and third dielectric layers each comprise a metal oxide.

33. The substrate of any preceding embodiment, wherein the first and third dielectric layers each comprise aluminum oxide.

34. The substrate of any preceding embodiment, wherein the first and third dielectric layers are each formed by atomic layer deposition.

35. The substrate of any one of any preceding embodiment, wherein the first and third dielectric layers each have a thickness of at least 10 nanometers.

36. The substrate of any preceding embodiment, wherein the first and third dielectric layers each have a thickness of about 10 to 20 nanometers.

37. The substrate of any one of any preceding embodiment, wherein the second dielectric layer comprises a non-metal oxide or a nitride.

38. The substrate of any preceding embodiment, wherein the second dielectric layer comprises silicon oxide.

39. The substrate of any preceding embodiment, wherein the second dielectric layer is formed by plasma enhanced chemical vapor deposition.

40. The substrate of any preceding embodiment, wherein the second dielectric layer has a thickness of at least 100 nanometers.

41. The substrate of any preceding embodiment, wherein the first dielectric layer has a top surface adjoining a bottom surface of the mesh ground electrode, and the third dielectric layer has a bottom surface adjoining a top surface of the mesh ground electrode.

42. The substrate of any preceding embodiment, wherein the first dielectric layer has a dielectric constant $\in1$, the third dielectric layer has a dielectric constant $\in3$, and $\in1$ is less than $\in3$.

43. The substrate of any preceding embodiment 42, wherein the second dielectric layer has a dielectric constant $\in2$, and $\in2$ is less than $\in3$.

44. The substrate of any preceding embodiment, wherein the mesh ground electrode comprises wires that are arranged in a lattice shape.

45. The substrate of any preceding embodiment, wherein the mesh ground electrode further comprises plates located on top of vertices formed by the wires of the mesh ground electrode.

46. The substrate of any preceding embodiment, wherein the wires of the mesh ground electrode have a substantially square shape or a substantially rectangular shape in cross-section.

47. The substrate of any preceding embodiment, wherein the wires of the mesh ground electrode, in cross section, have an average width and an average height, with the average height being at least 50 nm.

48. The substrate of any preceding embodiment, wherein the wires of the mesh ground electrode have a T-shape in cross section.

49. The substrate of any preceding embodiment, wherein the mesh ground electrode comprises a conductive metal.

50. The substrate of any preceding embodiment, wherein the mesh ground electrode comprises gold or aluminum.

51. The substrate of any preceding embodiment, wherein the mesh ground electrode comprises aluminum that has an oxidized outer surface.

52. The substrate of any preceding embodiment, wherein the mesh ground electrode has a linear fill factor $\beta$ less than or equal to 10%.

53. The substrate of any preceding embodiment, wherein wires of the mesh ground electrode have a pitch of about 200 microns to about 500 microns.

54. The substrate of any preceding embodiment, wherein the hydrophobic coating has a bottom surface that adjoins at least a portion of a top surface of the dielectric layer.

55. The substrate of any preceding embodiment, wherein the bottom surface of the hydrophobic coating adjoins a top surface of the mesh ground electrode.

56. The substrate of any preceding embodiment, wherein the hydrophobic coating comprises an organofluorine polymer having at least one perfluorinated segment.

57. The substrate of any preceding embodiment, wherein the organofluorine polymer comprises polytetrafluoro-ethylene (PTFE) or poly(2,3-difluoromethylenyl-perfluorotetrahydrofuran).

58. The substrate of any preceding embodiment, wherein the hydrophobic coating has a thickness of at least 20 nm.

59. The substrate of any preceding embodiment, wherein the hydrophobic layer comprises a densely packed monolayer of amphiphilic molecules covalently bonded to molecules of the dielectric layer.

60. The substrate of any preceding embodiment, wherein the amphiphilic molecules of the hydrophobic layer each comprise a siloxane group, and wherein the siloxane groups are covalently bonded to the molecules of the dielectric layer.

61. The substrate of any preceding embodiment, wherein the amphiphilic molecules of the hydrophobic layer each comprise a phosphonic acid group, and wherein the phosphonic acid groups are covalently bonded to the molecules of the dielectric layer.

62. The substrate of any preceding embodiment, wherein the amphiphilic molecules of the hydrophobic layer each comprise a thiol group, and wherein the thiol groups are covalently bonded to the molecules of the dielectric layer and/or the mesh ground electrode.

63. The substrate of any preceding embodiment, wherein the amphiphilic molecules of the hydrophobic layer comprise long-chain hydrocarbons.

64. The substrate of any preceding embodiment, wherein the long chain hydrocarbons are unbranched.

65. The substrate of any preceding embodiment, wherein the long-chain hydrocarbons comprise a chain of at least 10 carbons.

66. The substrate of any preceding embodiment, wherein the long-chain hydrocarbons comprise a chain of at least 16 carbons.

67. The substrate of any preceding embodiment, wherein the long-chain hydrocarbons comprise a chain of 16, 18, 20, or 22 carbons.

68. The substrate of any preceding embodiment, wherein the amphiphilic molecules of the hydrophobic layer comprise fluorinated carbon chains.

69. The substrate of any preceding embodiment, wherein the fluorinated carbon chains have the chemical formula $CF_3\text{-}(CF_2)_m\text{-}(CH_2)_n\text{-}$, wherein m is at least 2, n is at least 2, and m+n is at least 9.

70. The substrate of any preceding embodiment, wherein the fluorinated carbon chains have the chemical formula $CF_3\text{-}(CF_2)_m\text{-}(CH_2)_n\text{-}$, wherein m is at least 7 and n is at least 2.

71. The substrate of any preceding embodiment, wherein the hydrophobic layer has a thickness of less than 5 nanometers.

72. The substrate of any preceding embodiment, wherein the hydrophobic layer is patterned such that select regions are relatively hydrophilic compared to the remainder of the hydrophobic layer.

73. A microfluidic device comprising: a base comprising the substrate of any preceding embodiment; and walls disposed on a top surface of said base; wherein the base and the walls together define a microfluidic circuit.

74. The microfluidic device of any preceding embodiment further comprising a cover, wherein the cover is disposed on the walls.

75. The microfluidic device of any preceding embodiment, wherein the walls comprise a structural polymer.

76. The microfluidic device of any preceding embodiment, wherein the polymer comprises silicon.

77. The microfluidic device of any preceding embodiment, wherein the polymer comprises polydimethylsiloxane (PDMS) or photo-patternable silicone (PPS).

78. The microfluidic device of any preceding embodiment, wherein the cover comprises a structural polymer contained in the walls.

79. The microfluidic device of any preceding embodiment, wherein the walls comprises SU-8.

80. The microfluidic device of any preceding embodiment, wherein the walls have a height of at least 30 microns.

81. The microfluidic device of any preceding embodiment, wherein the walls have a height of about 50-100 microns.

82. The microfluidic device of any preceding embodiment, wherein the microfluidic circuit comprises one or more microchannels.

83. The microfluidic device of any preceding embodiment, wherein the microfluidic circuit comprises at least one microchannel and a plurality of chambers, wherein each chambers opens off of one of the microchannels.

84. A method of moving a droplet in a microfluidic device of any preceding embodiment, the method comprising: disposing a droplet of an aqueous solution on a top surface of a base of the microfluidic device; applying a AC voltage potential between the planar electrode and the mesh ground electrode; directing structured light at a position on the top surface of the base, in a location proximal to the droplet; and moving the structured light relative to the microfluidic device at a rate that induces the droplet to move across the top surface of the base.

85. The method of any preceding embodiment, wherein the droplet have a volume of 200 nL or less.

86. The method of any preceding embodiment, wherein the AC voltage potential is about 10 ppV to about 80 ppV.

87. The method of any preceding embodiment, wherein the AC voltage potential is about 30 ppV to about 50 ppV.

88. The method of any preceding embodiment, wherein the AC voltage potential has a frequency of about 1 kHz to about 1 MHz.

89. The method of any preceding embodiment, wherein the AC voltage potential has a frequency of about 5 kHz to about 100 kHz.

90. The method of any preceding embodiment, wherein the AC voltage potential has a frequency of about 5 kHz to about 20 kHz.

91. The method of any preceding embodiment, wherein the droplet has a conductivity of at least 1 mS/m.

92. The method of any preceding embodiment, wherein the structured light is moved relative to the microfluidic device at a rate of 0.1 cm/sec or greater.

93. A process for manipulating a droplet in a microfluidic device, the process comprising: filling some or all of a microfluidic circuit of a microfluidic device of any preceding embodiment with a first liquid medium; applying an AC voltage potential between a planar electrode and a mesh ground electrode of a base of the microfluidic device; introducing a first droplet of liquid into the microfluidic circuit, wherein the first droplet is immiscible in the first liquid medium; and moving the first droplet to a desired location within the microfluidic circuit by applying an electrowetting force to the first droplet.

94. The process of any preceding embodiment, wherein the first liquid medium is an oil.

95. The process of any preceding embodiment, wherein the first liquid medium is a silicone oil, a fluorinated oil, or a combination thereof.

96. The process of any preceding embodiment, wherein the applied AC voltage potential is about 10 ppV to about 80 ppV.

97. The process of any preceding embodiment, wherein the applied AC voltage potential is about 30 ppV to about 50 ppV.

98. The process of any preceding embodiment, wherein the applied AC voltage potential has a frequency of about 1 to 100 kHz.

99. The process of any preceding embodiment, wherein the applied AC voltage potential has a frequency of about 5 to 20 kHz.

100. The process of any preceding embodiment, wherein the microfluidic device comprises a droplet generator, and wherein the droplet generator introduces the first droplet into the microfluidic circuit.

101. The process of any preceding embodiment, wherein the first droplet comprises an aqueous solution.

102. The process of any preceding embodiment, wherein the first droplet comprises at least one micro-object.

103. The process of any preceding embodiment, wherein the at least one micro-object is a biological micro-object.

104. The process of any preceding embodiment, wherein the biological micro-object is a cell.

105. The process of any preceding embodiment, wherein the aqueous solution is a cell culture medium.

106. The process of any preceding embodiment, wherein the at least one micro-object is a capture bead having an affinity for a material of interest.

107. The process of any preceding embodiment, wherein the first droplet comprises two to twenty capture beads.

108. The process of any preceding embodiment, wherein the material of interest is a biological cell secretion.

109. The process of any preceding embodiment, wherein the material of interest is selected from the group consisting of DNA, genomic DNA, mitochondrial DNA, RNA, mRNA, miRNA, or any combination thereof.

110. The process of any preceding embodiment, wherein the first droplet comprises a reagent.

111. The process of any preceding embodiment, wherein the reagent is a cell lysis reagent.

112. The process of any preceding embodiment, wherein the reagent comprises a non-ionic detergent.

113. The process of any preceding embodiment, wherein the non-ionic detergent is at a concentration of less than 0.2%.

114. The process of any preceding embodiment, wherein the reagent is a proteolytic enzyme.

115. The process of any preceding embodiment, wherein the proteolytic enzyme is inactivatable.

116. The process of any preceding embodiment, further comprising: introducing a second droplet of liquid into the microfluidic circuit, wherein the liquid of the second droplet is immiscible in the first liquid medium but miscible with the liquid of the first droplet; moving the second droplet to a location within the microfluidic circuit adjacent to the first droplet by applying an electrowetting force to the second droplet; and merging the second droplet with the first droplet to form a combined droplet.

117. The process of any preceding embodiment, wherein the second droplet is merged with the first droplet by applying an electrowetting force to the second and/or the first droplet.

118. The process of any preceding embodiment, wherein the first droplet comprises a biological cell and the second droplet comprises a reagent.

119. The process of any preceding embodiment, wherein the reagent contained in the second droplet is selected from the group consist of a lysis buffer, a fluorescent label, and a luminescent assay reagent.

120. The process of any preceding embodiment, wherein the reagent contained in the second droplet is a lysis buffer, and wherein said biological cell is lysed upon merger of the first droplet and the second droplet.

121. The process of any preceding embodiment, wherein applying an electrowetting force to move and/or merge droplets comprises changing an effective electrowetting characteristic of a region of the top surface of the base of the microfluidic device proximal to the droplet(s).

122. The process of any preceding embodiment, wherein changing an effective electrowetting characteristic comprises activating electrowetting electrodes in a photoconductive layer of the base of the microfluidic device proximal to the droplet(s).

123. The process of any preceding embodiment, wherein activating the electrowetting electrodes in the photoconductive layer of the base of the microfluidic device proximal to the droplet(s) comprises directing a pattern of light into the photoconductive layer of the base of the microfluidic device proximal to the droplet(s).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed:

1. A substrate comprising:
a planar electrode;
a photoconductive layer;
a dielectric layer comprising at least a first layer of dielectric material;
a mesh ground electrode; and
a hydrophobic coating;
wherein the photoconductive layer is interposed between the planar electrode and the dielectric layer, with a bottom surface of the photoconductive layer adjoining a top surface of the planar electrode and a top surface of the photoconductive layer adjoining a bottom surface of the dielectric layer;
wherein the mesh ground electrode adjoins the dielectric layer, and wherein at least the first layer of dielectric material is interposed between the mesh ground electrode and the photoconductive layer;
wherein the planar electrode and the mesh ground electrode are configured to be connected to an AC voltage source; and
wherein, when the planar electrode and the mesh ground electrode are connected to opposing terminals of the AC voltage source, the substrate is capable of applying an opto-electrowetting (OEW) force to aqueous droplets in contact with the hydrophobic coating.

2. The substrate of claim 1, wherein the substrate forms all or part of the base of a microfluidic device.

3. The substrate of claim 1, wherein the photoconductive layer comprises hydrogenated amorphous silicon (a-Si:H).

4. The substrate of claim 1, wherein the dielectric layer comprises a metal oxide.

5. The substrate of claim 4, wherein the dielectric layer has a thickness of at least 125 nm and/or an impedance of about 10 kOhms to about 50 kOhms.

6. The substrate of claim 1, wherein the dielectric layer further comprises a second layer of dielectric material, with a bottom surface of the first layer of dielectric material adjoining the photoconductive layer and a top surface of the first layer of dielectric material adjoining a bottom surface of the second layer of dielectric material.

7. The substrate of claim 6, wherein the mesh ground electrode is interposed between the first layer of dielectric material and the second layer of dielectric material.

8. The substrate of claim 6, wherein the first layer of dielectric material and the second layer of dielectric material both comprise a metal oxide.

9. The substrate of claim 6, wherein the dielectric layer has a thickness of about 125 nm to about 175 nm and/or an impedance of about 10 kOhms to about 50 kOhms.

10. The substrate of claim 1, wherein the mesh ground electrode comprises wires that are arranged in a lattice shape.

11. The substrate of claim 10, wherein the mesh ground electrode comprises gold or aluminum.

12. The substrate of claim 10, wherein the mesh ground electrode comprises aluminum that has an oxidized outer surface.

13. The substrate of claim 10, wherein the mesh ground electrode has a linear fill factor β less than or equal to 10%.

14. The substrate of claim 13, wherein wires of the mesh ground electrode have a pitch of about 200 microns to about 500 microns.

15. The substrate of claim 1, wherein the hydrophobic coating has a bottom surface that adjoins at least a portion of a top surface of the dielectric layer, and optionally, wherein the bottom surface of the hydrophobic coating further adjoins a top surface of the mesh ground electrode.

16. The substrate of claim 15, wherein the hydrophobic coating comprises an organofluorine polymer having at least one perfluorinated segment.

17. The substrate of claim 15, wherein the hydrophobic coating comprises a densely packed monolayer of amphiphilic molecules covalently bonded to molecules of the dielectric layer.

18. The substrate of claim 17, wherein the amphiphilic molecules of the monolayer each comprise:
- a siloxane group, and wherein the siloxane groups are covalently bonded to the molecules of the dielectric layer;
- a phosphonic acid group, and wherein the phosphonic acid groups are covalently bonded to the molecules of the dielectric layer; or
- a thiol group, and wherein the thiol groups are covalently bonded to the molecules of the dielectric layer.

19. The substrate of claim 18, wherein the amphiphilic molecules of the monolayer comprise long-chain hydrocarbons having a chain of at least 16 carbons.

20. The substrate of claim 18, wherein the amphiphilic molecules of the monolayer comprise fluorinated carbon chains.

21. The substrate of claim 20, wherein the fluorinated carbon chains have the chemical formula CF3-(CF2)m-(CH2)n-, wherein m is at least 2, n is at least 2, and m+n is at least 9.

22. The substrate of claim 18, wherein the hydrophobic coating is patterned such that select regions are relatively hydrophilic compared to the remainder of the hydrophobic coating.

23. A microfluidic device comprising:
- a base comprising the substrate of claim 1; and
- walls disposed on a top surface of said base;
- wherein the base and the walls together define a microfluidic circuit.

24. The microfluidic device of claim 23 further comprising a cover, wherein the cover is disposed on the walls.

25. The microfluidic device of claim 23, wherein the microfluidic circuit comprises at least one microchannel and a plurality of chambers, wherein each chamber opens off of one microchannel of the at least one microchannel.

26. A method of moving a droplet in a microfluidic device of claim 23, the method comprising:
- disposing a droplet of an aqueous solution on a top surface of the base of the microfluidic device;
- applying a AC voltage potential between the planar electrode and the mesh ground electrode;
- directing structured light at a position on the top surface of the base, in a location proximal to the droplet; and
- moving the structured light relative to the microfluidic device at a rate that induces the droplet to move across the top surface of the base.

27. The method of claim 26, wherein the AC voltage potential is about 10 ppV to about 80 ppV.

28. The method of claim 27, wherein the AC voltage potential has a frequency of about 1 kHz to about 1 MHz.

29. The method of claim 27, wherein the AC voltage potential has a frequency of about 5 kHz to about 100 kHz.

30. The method of claim 27, wherein the AC voltage potential is about 30 ppV to about 50 ppV.

* * * * *